(12) United States Patent
Nicholas

(10) Patent No.: US 12,310,591 B2
(45) Date of Patent: May 27, 2025

(54) SURGICAL STAPLING DEVICE WITH FLEXIBLE SHAFT

(71) Applicant: Covidien LP, Mansfield, MA (US)

(72) Inventor: David A. Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/267,480

(22) PCT Filed: Dec. 7, 2021

(86) PCT No.: PCT/US2021/062106
§ 371 (c)(1),
(2) Date: Jun. 15, 2023

(87) PCT Pub. No.: WO2022/132488
PCT Pub. Date: Jun. 23, 2022

(65) Prior Publication Data
US 2024/0058006 A1 Feb. 22, 2024

Related U.S. Application Data

(60) Provisional application No. 63/125,436, filed on Dec. 15, 2020.

(51) Int. Cl.
*A61B 17/064* (2006.01)
*A61B 17/115* (2006.01)

(52) U.S. Cl.
CPC ................................ *A61B 17/1155* (2013.01)

(58) Field of Classification Search
CPC . A61B 17/068; A61B 17/0686; A61B 17/115; A61B 17/1155
See application file for complete search history.

(56) References Cited

U.S. PATENT DOCUMENTS

| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |

(Continued)

FOREIGN PATENT DOCUMENTS

| CA | 908529 A | 8/1972 |
| CA | 2805365 A1 | 8/2013 |

(Continued)

OTHER PUBLICATIONS

International Search Report for Application No. PCT/US2021/062106 dated Mar. 15, 2022.

(Continued)

*Primary Examiner* — Eyamindae C Jallow

(57) ABSTRACT

A surgical stapling device that includes an adapter assembly that has a flexible outer tube, and a tool assembly that is supported on the flexible outer tube having an anvil assembly and a shell assembly that supports an annular staple cartridge. The shell assembly includes a mechanism for approximating the anvil assembly with the shell assembly over two clamping stages to minimize forces transferred to the flexible outer tube of the adapter assembly during clamping. The shell assembly also includes a mechanism for minimizing firing forces required to eject staples from the staple cartridge.

20 Claims, 24 Drawing Sheets

(56) References Cited

U.S. PATENT DOCUMENTS

| | | |
|---|---|---|
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |

(56) References Cited

U.S. PATENT DOCUMENTS

| | | |
|---|---|---|
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |

(56) References Cited

U.S. PATENT DOCUMENTS

| | | | |
|---|---|---|---|
| 7,931,183 B2 | 4/2011 | Orban, III | |
| 7,938,307 B2 | 5/2011 | Bettuchi | |
| 7,942,302 B2 | 5/2011 | Roby et al. | |
| 7,947,034 B2 * | 5/2011 | Whitman | A61B 17/1631 606/1 |
| 7,951,166 B2 | 5/2011 | Orban, III et al. | |
| 7,959,050 B2 | 6/2011 | Smith et al. | |
| 7,967,181 B2 | 6/2011 | Viola et al. | |
| 7,975,895 B2 | 7/2011 | Milliman | |
| 8,002,795 B2 | 8/2011 | Beetel | |
| 8,006,701 B2 | 8/2011 | Bilotti et al. | |
| 8,006,889 B2 | 8/2011 | Adams et al. | |
| 8,011,551 B2 | 9/2011 | Marczyk et al. | |
| 8,011,554 B2 | 9/2011 | Milliman | |
| 8,016,177 B2 | 9/2011 | Bettuchi et al. | |
| 8,016,858 B2 | 9/2011 | Whitman | |
| 8,020,741 B2 | 9/2011 | Cole et al. | |
| 8,025,199 B2 | 9/2011 | Whitman et al. | |
| 8,028,885 B2 | 10/2011 | Smith et al. | |
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky | |
| 8,096,458 B2 | 1/2012 | Hessler | |
| 8,096,460 B2 * | 1/2012 | Blier | A61B 17/07207 227/176.1 |
| 8,109,426 B2 | 2/2012 | Milliman et al. | |
| 8,109,427 B2 | 2/2012 | Orban, III | |
| 8,113,405 B2 | 2/2012 | Milliman | |
| 8,113,406 B2 | 2/2012 | Holsten et al. | |
| 8,113,407 B2 | 2/2012 | Holsten et al. | |
| 8,123,103 B2 | 2/2012 | Milliman | |
| 8,128,645 B2 | 3/2012 | Sonnenschein et al. | |
| 8,132,703 B2 | 3/2012 | Milliman et al. | |
| 8,136,712 B2 | 3/2012 | Zingman | |
| 8,146,790 B2 | 4/2012 | Milliman | |
| 8,146,791 B2 | 4/2012 | Bettuchi et al. | |
| 8,181,838 B2 | 5/2012 | Milliman et al. | |
| 8,192,460 B2 | 6/2012 | Orban, III et al. | |
| 8,201,720 B2 | 6/2012 | Hessler | |
| 8,203,782 B2 | 6/2012 | Brueck et al. | |
| 8,211,130 B2 | 7/2012 | Viola | |
| 8,225,799 B2 | 7/2012 | Bettuchi | |
| 8,225,981 B2 | 7/2012 | Criscuolo et al. | |
| 8,231,041 B2 | 7/2012 | Marczyk et al. | |
| 8,231,042 B2 | 7/2012 | Hessler et al. | |
| 8,257,391 B2 | 9/2012 | Orban, III et al. | |
| 8,267,301 B2 | 9/2012 | Milliman et al. | |
| 8,272,552 B2 | 9/2012 | Holsten et al. | |
| 8,276,802 B2 | 10/2012 | Kostrzewski | |
| 8,281,975 B2 | 10/2012 | Criscuolo et al. | |
| 8,286,845 B2 | 10/2012 | Perry et al. | |
| 8,308,045 B2 | 11/2012 | Bettuchi et al. | |
| 8,312,885 B2 | 11/2012 | Bettuchi et al. | |
| 8,313,014 B2 | 11/2012 | Bettuchi | |
| 8,317,073 B2 | 11/2012 | Milliman et al. | |
| 8,317,074 B2 | 11/2012 | Ortiz et al. | |
| 8,322,590 B2 | 12/2012 | Patel et al. | |
| 8,328,060 B2 | 12/2012 | Jankowski et al. | |
| 8,328,062 B2 | 12/2012 | Viola | |
| 8,328,063 B2 | 12/2012 | Milliman et al. | |
| 8,343,185 B2 | 1/2013 | Milliman et al. | |
| 8,353,438 B2 | 1/2013 | Baxter, III et al. | |
| 8,353,439 B2 | 1/2013 | Baxter, III et al. | |
| 8,353,930 B2 | 1/2013 | Heinrich et al. | |
| 8,360,295 B2 | 1/2013 | Milliman et al. | |
| 8,365,974 B2 | 2/2013 | Milliman | |
| 8,403,942 B2 | 3/2013 | Milliman et al. | |
| 8,408,441 B2 | 4/2013 | Wenchell et al. | |
| 8,413,870 B2 | 4/2013 | Pastorelli et al. | |
| 8,413,872 B2 | 4/2013 | Patel | |
| 8,418,905 B2 | 4/2013 | Milliman | |
| 8,418,909 B2 | 4/2013 | Kostrzewski | |
| 8,424,535 B2 | 4/2013 | Hessler et al. | |
| 8,424,741 B2 | 4/2013 | McGuckin, Jr. et al. | |
| 8,430,291 B2 | 4/2013 | Heinrich et al. | |
| 8,430,292 B2 | 4/2013 | Patel et al. | |
| 8,444,549 B2 * | 5/2013 | Viola | A61B 1/0055 600/117 |
| 8,453,910 B2 | 6/2013 | Bettuchi et al. | |
| 8,453,911 B2 | 6/2013 | Milliman et al. | |
| 8,479,968 B2 | 7/2013 | Hodgkinson et al. | |
| 8,485,414 B2 | 7/2013 | Criscuolo et al. | |
| 8,490,853 B2 | 7/2013 | Criscuolo et al. | |
| 8,511,533 B2 | 8/2013 | Viola et al. | |
| 8,551,138 B2 | 10/2013 | Orban, III et al. | |
| 8,567,655 B2 | 10/2013 | Nalagatla et al. | |
| 8,579,178 B2 | 11/2013 | Holsten et al. | |
| 8,590,763 B2 | 11/2013 | Milliman | |
| 8,590,764 B2 | 11/2013 | Hartwick et al. | |
| 8,608,047 B2 | 12/2013 | Holsten et al. | |
| 8,616,428 B2 | 12/2013 | Milliman et al. | |
| 8,616,429 B2 | 12/2013 | Viola | |
| 8,622,275 B2 | 1/2014 | Baxter, III et al. | |
| 8,627,995 B2 | 1/2014 | Smith et al. | |
| 8,631,993 B2 | 1/2014 | Kostrzewski | |
| 8,636,187 B2 | 1/2014 | Hueil et al. | |
| 8,640,940 B2 | 2/2014 | Ohdaira | |
| 8,646,674 B2 | 2/2014 | Schulte et al. | |
| 8,662,370 B2 | 3/2014 | Takei | |
| 8,663,258 B2 | 3/2014 | Bettuchi et al. | |
| 8,672,207 B2 | 3/2014 | Shelton, IV et al. | |
| 8,672,931 B2 | 3/2014 | Goldboss et al. | |
| 8,672,951 B2 | 3/2014 | Smith et al. | |
| 8,678,264 B2 | 3/2014 | Racenet et al. | |
| 8,679,137 B2 | 3/2014 | Bauman et al. | |
| 8,684,248 B2 | 4/2014 | Milliman | |
| 8,684,250 B2 | 4/2014 | Bettuchi et al. | |
| 8,684,251 B2 | 4/2014 | Rebuffat et al. | |
| 8,684,252 B2 | 4/2014 | Patel et al. | |
| 8,695,864 B1 | 4/2014 | Hausen | |
| 8,708,212 B2 | 4/2014 | Williams | |
| 8,733,611 B2 | 5/2014 | Milliman | |
| 8,733,615 B2 | 5/2014 | Nalagatla et al. | |
| 8,746,531 B2 | 6/2014 | Wenchell et al. | |
| 8,746,532 B2 | 6/2014 | Nalagatla et al. | |
| 8,783,543 B2 | 7/2014 | Shelton, IV et al. | |
| 8,789,737 B2 | 7/2014 | Hodgkinson et al. | |
| 8,800,838 B2 | 8/2014 | Shelton, IV | |
| 8,800,841 B2 | 8/2014 | Ellerhorst et al. | |
| 8,801,734 B2 | 8/2014 | Shelton, IV et al. | |
| 8,801,735 B2 | 8/2014 | Shelton, IV et al. | |
| 8,821,523 B2 | 9/2014 | Heinrich et al. | |
| 8,827,903 B2 | 9/2014 | Shelton, IV et al. | |
| 8,833,629 B2 | 9/2014 | Nalagatla et al. | |
| 8,840,004 B2 | 9/2014 | Holsten et al. | |
| 8,844,792 B2 | 9/2014 | Viola | |
| 8,845,661 B2 | 9/2014 | D'Arcangelo et al. | |
| 8,870,911 B2 | 10/2014 | Williams et al. | |
| 8,875,974 B2 | 11/2014 | Rebuffat et al. | |
| 8,893,948 B2 | 11/2014 | Williams | |
| 8,910,847 B2 | 12/2014 | Nalagatla et al. | |
| 8,925,785 B2 | 1/2015 | Holsten et al. | |
| 8,925,786 B2 | 1/2015 | Holsten et al. | |
| 8,967,448 B2 | 3/2015 | Carter et al. | |
| 8,978,955 B2 | 3/2015 | Aronhalt et al. | |
| 9,010,608 B2 | 4/2015 | Casasanta, Jr. et al. | |
| 9,010,612 B2 | 4/2015 | Stevenson et al. | |
| 9,016,540 B2 | 4/2015 | Whitman et al. | |
| 9,023,014 B2 | 5/2015 | Chowaniec et al. | |
| 9,033,204 B2 | 5/2015 | Shelton, IV et al. | |
| 9,055,943 B2 | 6/2015 | Zemlok et al. | |
| 9,095,340 B2 | 8/2015 | Felder et al. | |
| 9,113,871 B2 | 8/2015 | Milliman et al. | |
| 9,113,877 B1 | 8/2015 | Whitman et al. | |
| 9,113,883 B2 | 8/2015 | Aronhalt et al. | |
| 9,113,884 B2 | 8/2015 | Shelton, IV et al. | |
| 9,113,885 B2 | 8/2015 | Hodgkinson et al. | |
| 9,125,654 B2 | 9/2015 | Aronhalt et al. | |
| 9,155,536 B1 | 10/2015 | Hausen et al. | |
| 9,161,757 B2 | 10/2015 | Bettuchi | |
| 9,204,881 B2 | 12/2015 | Penna | |

(56) References Cited

U.S. PATENT DOCUMENTS

| | | |
|---|---|---|
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2005/0187576 A1* | 8/2005 | Whitman ............ A61B 17/1155 227/176.1 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |

(56) References Cited

U.S. PATENT DOCUMENTS

| | | |
|---|---|---|
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2017/0128068 A1 | 5/2017 | Zhang et al. |
| 2017/0340351 A1 | 11/2017 | Sgroi, Jr. |
| 2018/0125495 A1 | 5/2018 | Sgroi, Jr. |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| EP | 3412225 A1 | 12/2018 |
| EP | 3549545 A2 | 10/2019 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9835614 A1 | 8/1998 |
| WO | 0154594 A1 | 8/2001 |
| WO | 02080781 A2 | 10/2002 |
| WO | 2004032766 A2 | 4/2004 |
| WO | 2004047654 A2 | 6/2004 |
| WO | 2008107918 A1 | 9/2008 |
| WO | 2013087092 A1 | 6/2013 |
| WO | 2019130087 A1 | 7/2019 |

OTHER PUBLICATIONS

Written Opinion for Application No. PCT/US2021/062106 dated Mar. 15, 2022.

* cited by examiner

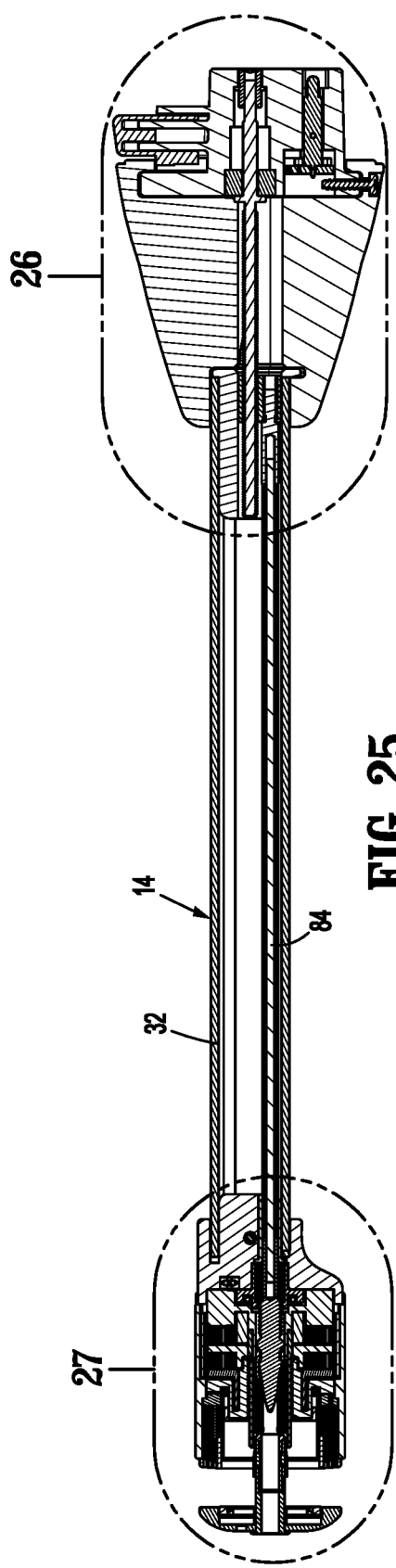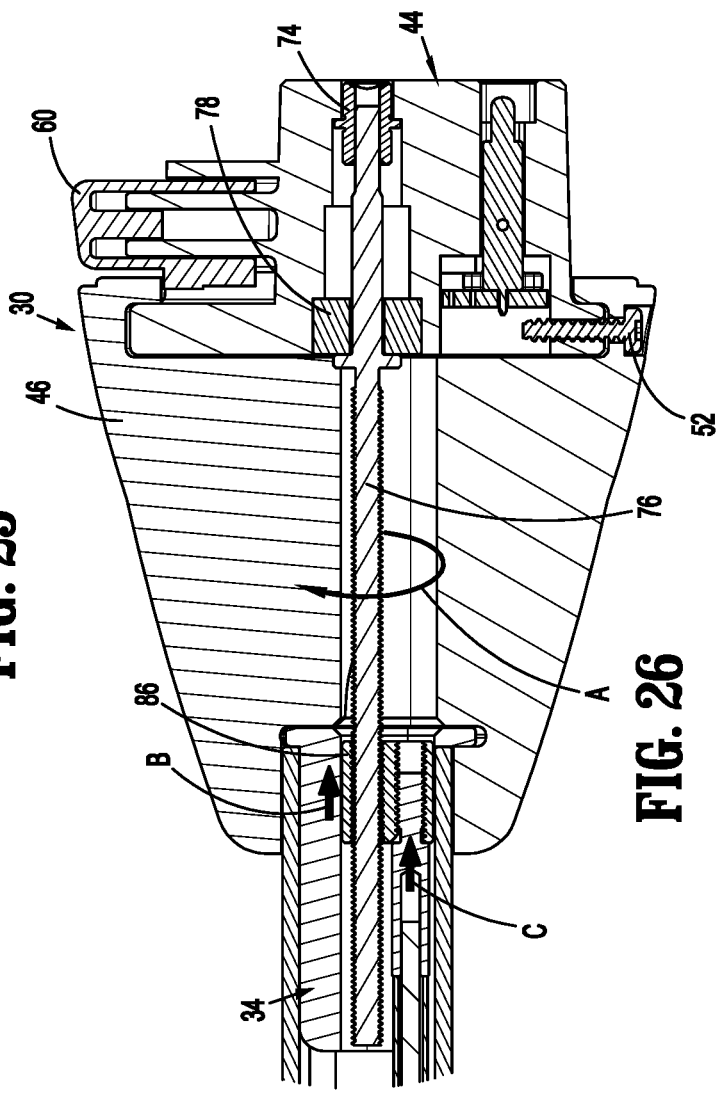
FIG. 25
FIG. 26

SURGICAL STAPLING DEVICE WITH FLEXIBLE SHAFT

CROSS-REFERENCE TO RELATED APPLICATION

This application claims the benefit of and priority to U.S. Provisional Patent Application No. 63/125,436, filed Dec. 15, 2020, the entire contents of which is incorporated by reference herein.

FIELD

This disclosure is directed to stapling devices and, more particularly, to endoscopic stapling devices with flexible shafts that support an end effector.

BACKGROUND

Surgical stapling devices for performing surgical procedures endoscopically are well known and are commonly used to reduce patient trauma and shorten patient recovery times. Typically, an endoscopic stapling device includes a handle assembly, a rigid elongate body that extends distally from the handle assembly, and an end effector including a tool assembly that is supported on a distal portion of the elongate body. The handle assembly is coupled to the end effector by drive mechanisms that extend through the elongate body and allow a clinician to control operation of the end effector remotely via the handle assembly.

Surgical stapling devices for endoscopic use are available in a variety of configurations including linear and circular. Circular stapling devices are commonly used to perform anastomoses after resections of the large bowel, i.e., colectomies. In a large percentage of colectomy procedures, the portion of the colon that must be resected is in the ascending colon or the transverse colon which cannot be easily accessed by a circular stapling device having a rigid shaft. As such, these procedures are typically performed during an open colectomy procedure which result in increased patient trauma and recovery time.

A continuing need exists in the medical arts for a stapling device having a flexible shaft for accessing a surgical site.

SUMMARY

This disclosure is directed to a surgical stapling device that includes an adapter assembly having a flexible outer tube, and a tool assembly supported on the flexible outer tube having an anvil assembly and a shell assembly that supports an annular staple cartridge. The shell assembly includes a mechanism for approximating the anvil assembly with the shell assembly over two clamping stages to minimize forces transferred to the flexible outer tube of the adapter assembly. The shell assembly also includes a mechanism for minimizing firing forces required to eject staples from the staple cartridge.

In one aspect of this disclosure, a shell assembly includes a shell housing that defines a cavity, a staple cartridge that is supported on the shell housing, a segmented pusher assembly, and a pusher drive. The staple cartridge defines staple receiving slots that receive staples. The segmented pusher assembly is positioned within the cavity of the shell housing and includes a plurality of pushers arranged in an annular configuration. Each of the pushers includes an angled cam surface and that is movable independently of other pushers of the plurality of pushers from a retracted position to an advanced position. The pusher drive is supported within the cavity of the shell housing and includes a cam member. The pusher drive is rotatable to move the cam member into sequential engagement with the cam surfaces of the plurality of pushers of the segmented pusher to sequentially advance the plurality of pushers of the segmented pusher from their retracted positions to their advanced positions to eject staples from the staple cartridge.

In aspects of the disclosure, the shell assembly includes a threaded spline tube that is secured within the shell housing, and the pusher drive is rotatably positioned about the threaded spline tube.

In some aspects of the disclosure, the pusher drive includes a central hub that includes an inner threaded surface and the threaded spline tube has an outer surface that includes threads.

In certain aspects of the disclosure, the threads on the outer surface of the threaded spline tube are engaged with the inner threaded surface of the pusher drive such that rotation of the pusher drive about the threaded spline tube causes longitudinal movement of the pusher drive about the threaded spline tube.

In aspects of the disclosure, the cam surfaces of the plurality of pushers are longitudinally offset from each other in stepped fashion to compensate for the longitudinal movement of the pusher drive.

In some aspects of the disclosure, the shell assembly includes a sun gear, a first planetary gear set, a spider input gear, a second planetary gear set, and a spider output gear.

In certain aspects of the disclosure, the first planetary gear set is rotatably supported on the spider input gear, the second planetary gear set is supported on the spider output gear, and the sun gear is engaged with the first planetary gear set such that rotation of the sun gear causes rotation of the spider output gear.

In aspects of the disclosure, the shell assembly includes a ring gear that is fixedly secured to the shell housing.

In some aspects of the disclosure, the ring gear engages with the first and second planetary gear sets such that rotation of the first planetary gear set causes rotation of the spider input gear and rotation of the second planetary gear set causes rotation of the spider output gear.

In aspects of the disclosure, the pusher drive is rotatably fixed to the spider output gear.

In some aspects of the disclosure, the spider output gear includes a central hub that defines a through bore, and the central hub of the spider output gear has an inner surface that includes longitudinally extending ribs.

In certain aspects of the disclosure, the central hub of the pusher drive defines longitudinally channels that receive the longitudinally extending ribs of the central hub of the spider output gear to rotatably fix the spider output gear to the pusher drive.

In another aspect of the disclosure, a surgical stapling device includes an adapter assembly and a tool assembly. The adapter assembly includes a flexible outer tube, a first drive assembly, and a second drive assembly. The flexible outer tube has a proximal portion and a distal portion. The first drive assembly extends through the flexible outer tube and includes a flexible approximation link having a proximal portion and a distal portion and an anvil retainer secured to the distal portion of the flexible approximation link. The anvil retainer includes a threaded outer portion. The second drive assembly extends through the flexible outer tube and includes a flexible drive shaft having a proximal portion and a distal portion, and an input gear secured to the distal portion of the flexible drive shaft. The tool assembly is secured to the distal portion of the flexible outer tube and includes an anvil assembly and a shell assembly. The anvil assembly includes an anvil head and an anvil shaft secured to the anvil head. The shell assembly includes a housing and a clamp gear supported within the housing of the shell assembly. The clamp gear is engaged with the input gear of the second drive assembly. Activation of the first drive assembly through a first clamping stage retracts the flexible articulation link to move the anvil retainer proximally to move the anvil assembly from an open position to a partially clamped position in which the threaded outer portion of the anvil retainer is engaged with the clamp gear. Activation of the second drive assembly through a second clamping stage moves the anvil retainer further proximally to move the anvil assembly from the partially clamped position to a fully clamped position.

In aspects of the disclosure, the shell assembly includes a clamp nut that is supported within the clamp gear and defines a threaded bore.

In some aspects of the disclosure, the threaded outer portion of the anvil retainer is received within the threaded bore of the clamp nut when the anvil assembly is in the partially retracted position.

In certain aspects of the disclosure, the anvil shaft is releasably coupled to the anvil retainer.

In aspects of the disclosure, the stapling device includes a handle assembly, and the proximal portion of the adapter assembly is coupled to the handle assembly.

Another aspect of the disclosure is directed to a surgical stapling device including an adapter assembly and a tool assembly. The adapter assembly includes a flexible outer tube, a first drive assembly, and a second drive assembly. The flexible outer tube has a proximal portion and a distal portion. The first drive assembly extends through the flexible outer tube and includes a flexible approximation link having a proximal portion and a distal portion. An anvil retainer is secured to the distal portion of the flexible approximation link and includes a threaded outer portion. The second drive assembly extends through the flexible outer tube and includes a flexible drive shaft having a proximal portion and a distal portion. An input gear is secured to the distal portion of the flexible drive shaft. The tool assembly is secured to the distal portion of the flexible outer tube and includes an anvil assembly and a shell assembly. The anvil assembly includes an anvil head and an anvil shaft secured to the anvil head. The shell assembly includes a shell housing that defines a cavity, a staple cartridge supported on the shell housing, a segmented pusher assembly, a pusher drive, and a clamp gear supported within the housing of the shell assembly. The clamp gear is engaged with the input gear of the second drive assembly. The staple cartridge defines staple receiving slots that receive staples. The segmented pusher assembly is positioned within the cavity of the shell housing and includes a plurality of pushers that are arranged in an annular configuration. Each of the pushers includes an angled cam surface and is movable independently of other pushers of the plurality of pushers from a retracted position to an advanced position to eject the staples from the staple cartridge. The pusher drive is supported within the cavity of the shell housing and includes a cam member. The pusher drive is rotatable to move the cam member into sequential engagement with the cam surfaces of the plurality of pushers of the segmented pusher to sequentially advance the plurality of pushers of the segmented pusher from their retracted positions to their advanced positions. Activation of the first drive assembly through a first clamping stage retracts the flexible articulation link to move the anvil retainer proximally to move the anvil assembly from an open position to a partially clamped position in which the threaded outer portion of the anvil retainer is engaged with the clamp gear. Activation of the second drive assembly through a second clamping stage moves the anvil retainer further proximally to move the anvil assembly from the partially clamped position to a fully clamped position.

Other aspects of the disclosure will be appreciated from the following description.

BRIEF DESCRIPTION OF THE DRAWINGS

Various exemplary aspects of the disclosed surgical stapling device are described herein below with reference to the drawings, wherein:

FIG. 25 is a cross-sectional view of the surgical stapling device shown in FIG. 3 as the tool assembly moves towards the clamped position;

FIG. 26 is an enlarged view of the indicated area of detail shown in FIG. 25;

DETAILED DESCRIPTION

Figure 1:
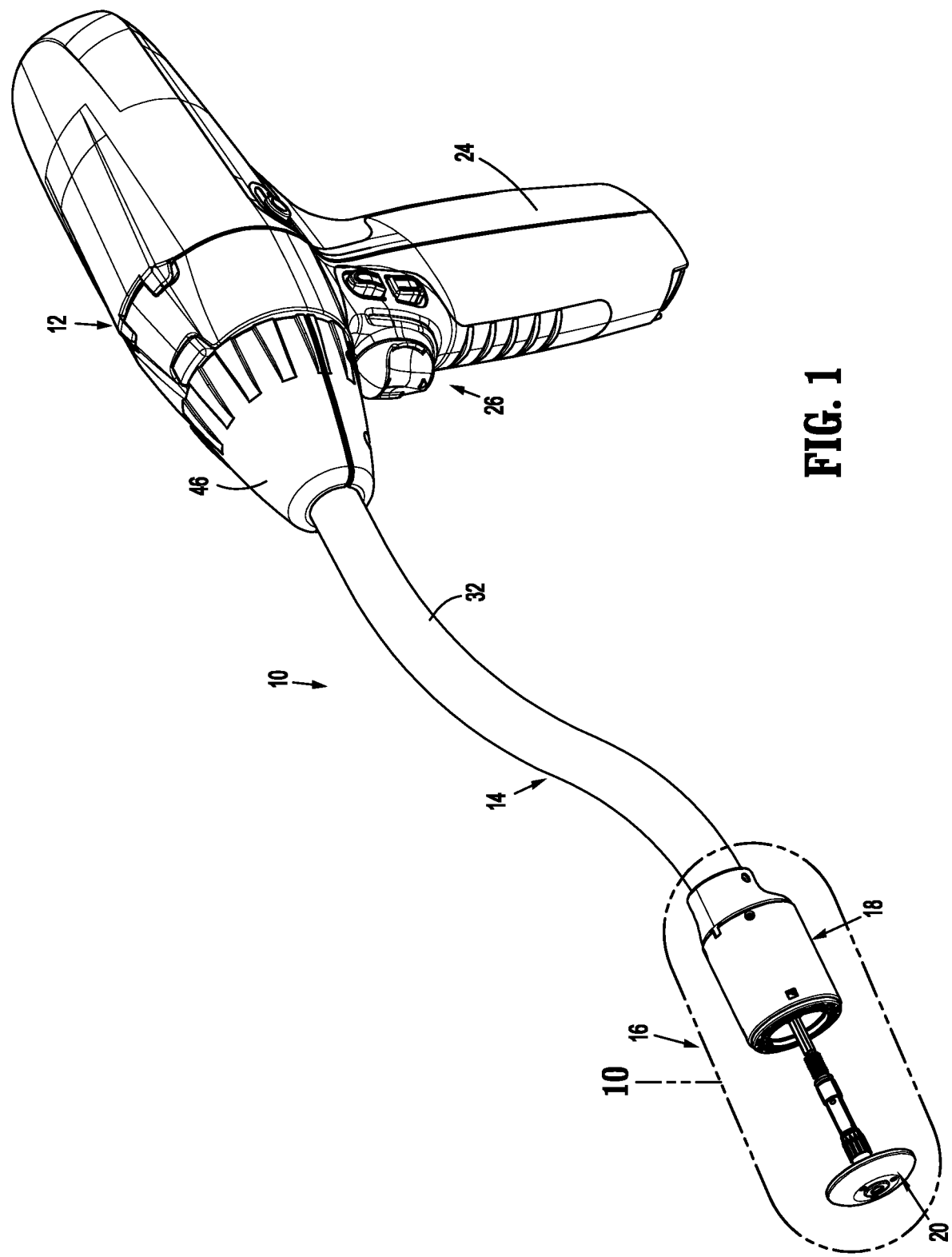
FIG. 1 is a side perspective view of a surgical stapling device including exemplary aspects of the disclosure with a tool assembly in an open position.
Figure 2:
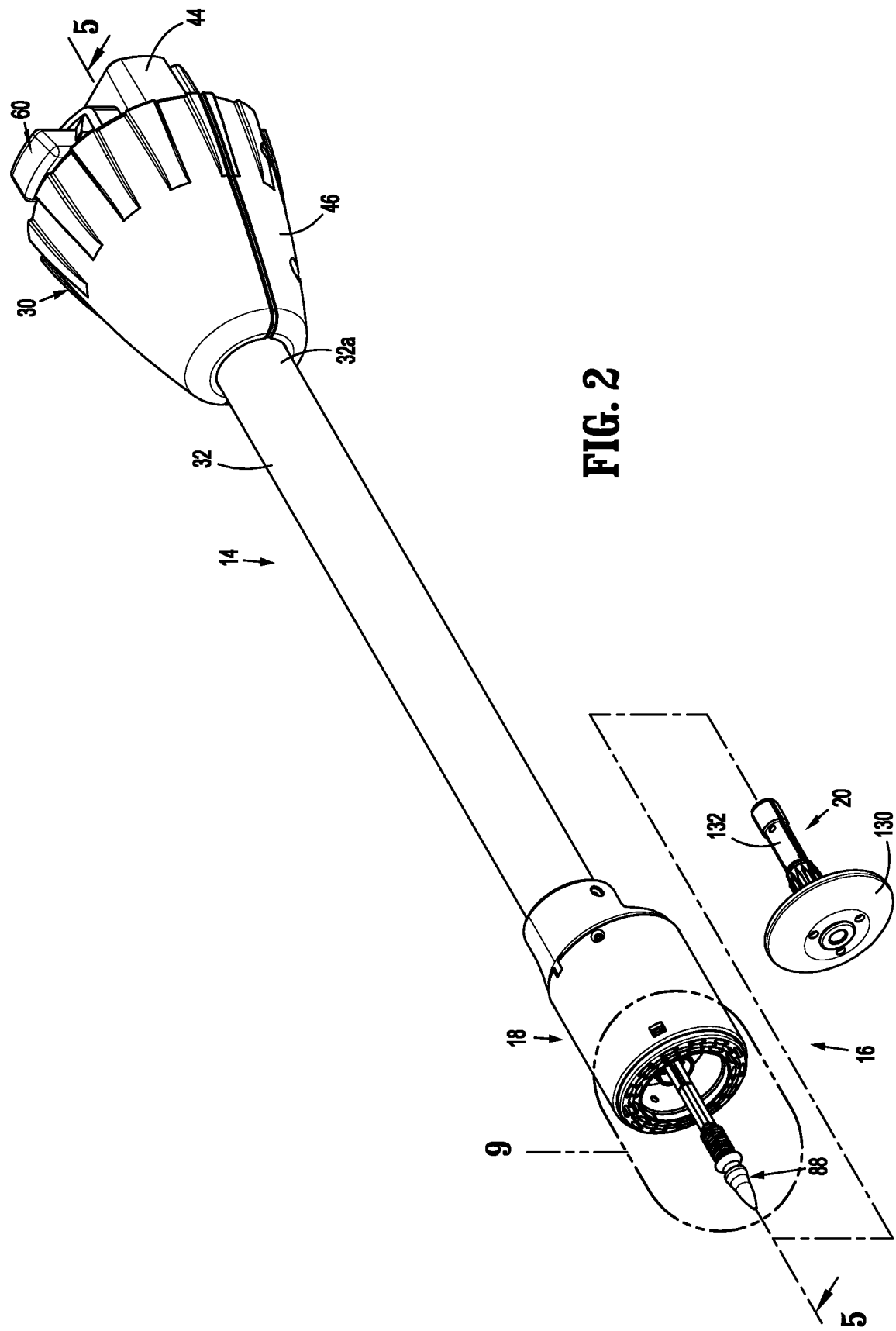
FIG. 2 is a side perspective view of the tool assembly and an adapter assembly of the surgical stapling device shown in FIG. 1 with an anvil assembly of the tool assembly separated from an anvil retainer of the stapling device.
Figure 3:
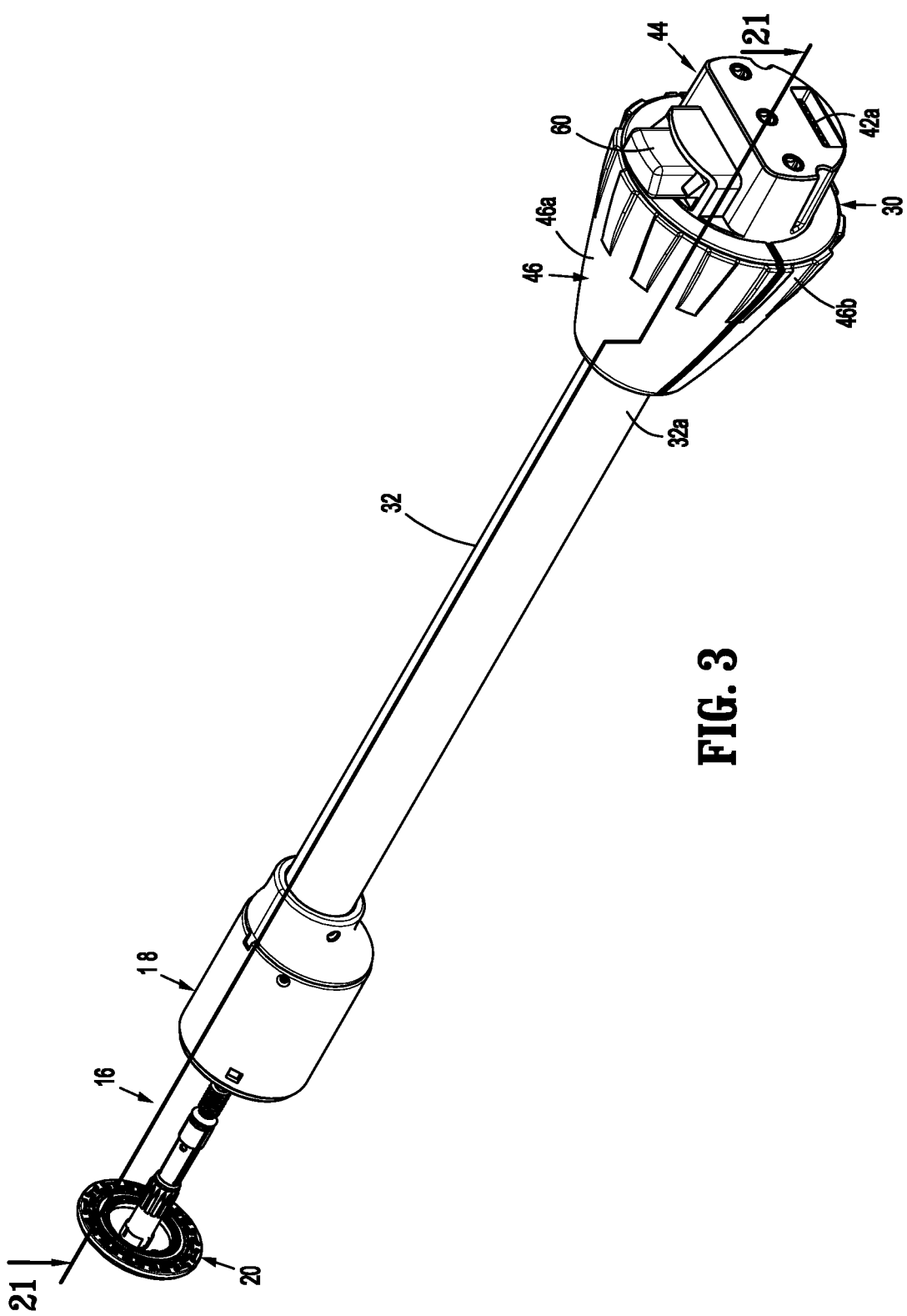
FIG. 3 is a side perspective view of the distal portion of the surgical stapling device shown in FIG. 2 with the anvil assembly coupled to the anvil retainer and the tool assembly in the open position.

The disclosed surgical stapling device will now be described in detail with reference to the drawings in which like reference numerals designate identical or corresponding elements in each of the several views. However, it is to be understood that the aspects of the disclosure described herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally to refer to endoscopic, laparoscopic, arthroscopic, and/or any other procedure conducted through small diameter incision or cannula. Further, the term "clinician" is used generally to refer to medical personnel including doctors, nurses, and support personnel.

Figure 34:
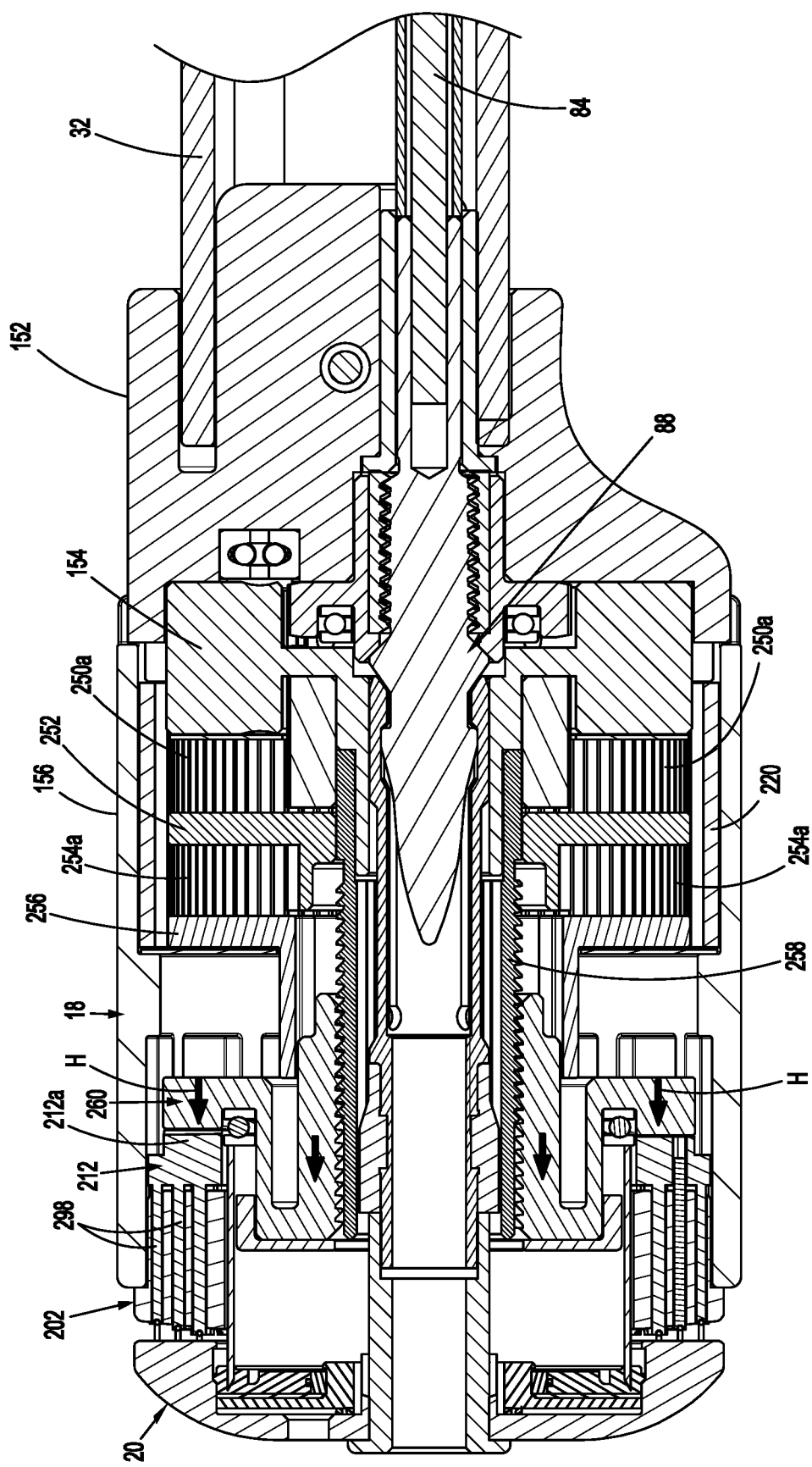
FIG. 34 is a side cross-sectional view of the tool assembly shown in FIG. 28 with the stapling device in the fired condition.

FIG. 1 illustrates a circular stapling device shown generally as stapling device 10 including exemplary aspects of the disclosure. The stapling device 10 includes a handle assembly 12, an adapter assembly 14, and a tool assembly 16. The tool assembly 16 includes a shell assembly 18 and an anvil assembly 20 that is supported for movement in relation to the shell assembly 18 between an open position (FIG. 1) and a clamped position (FIG. 34). The handle assembly 12 includes a stationary grip 24 that supports actuation buttons 26 for controlling operation of various functions of the stapling device 10 including approximation of the shell and anvil assemblies 18, 20, firing of staples from the reload assembly 18, and cutting or coring of tissue.

The stapling device 10 is an electrically powered stapling device. As such, the handle assembly 12 may support a motor or motors, control circuitry, and a battery or battery pack (not shown) for driving various mechanisms of the adapter assembly 14 to facilitate approximation of the shell and anvil assemblies 18, 20, firing of staples from the reload assembly 18, and cutting or coring of tissue. Examples of electrically powered stapling devices including a handle assembly suitable for use with the disclosed stapling device 10 can be found in U.S. Pat. No. 9,055,943 (the '943 Patent), U.S. Pat. No. 9,023,014 (the '014 Patent), and U.S. Publication Nos. 2018/0125495, and 2017/0340351.

Figure 4:
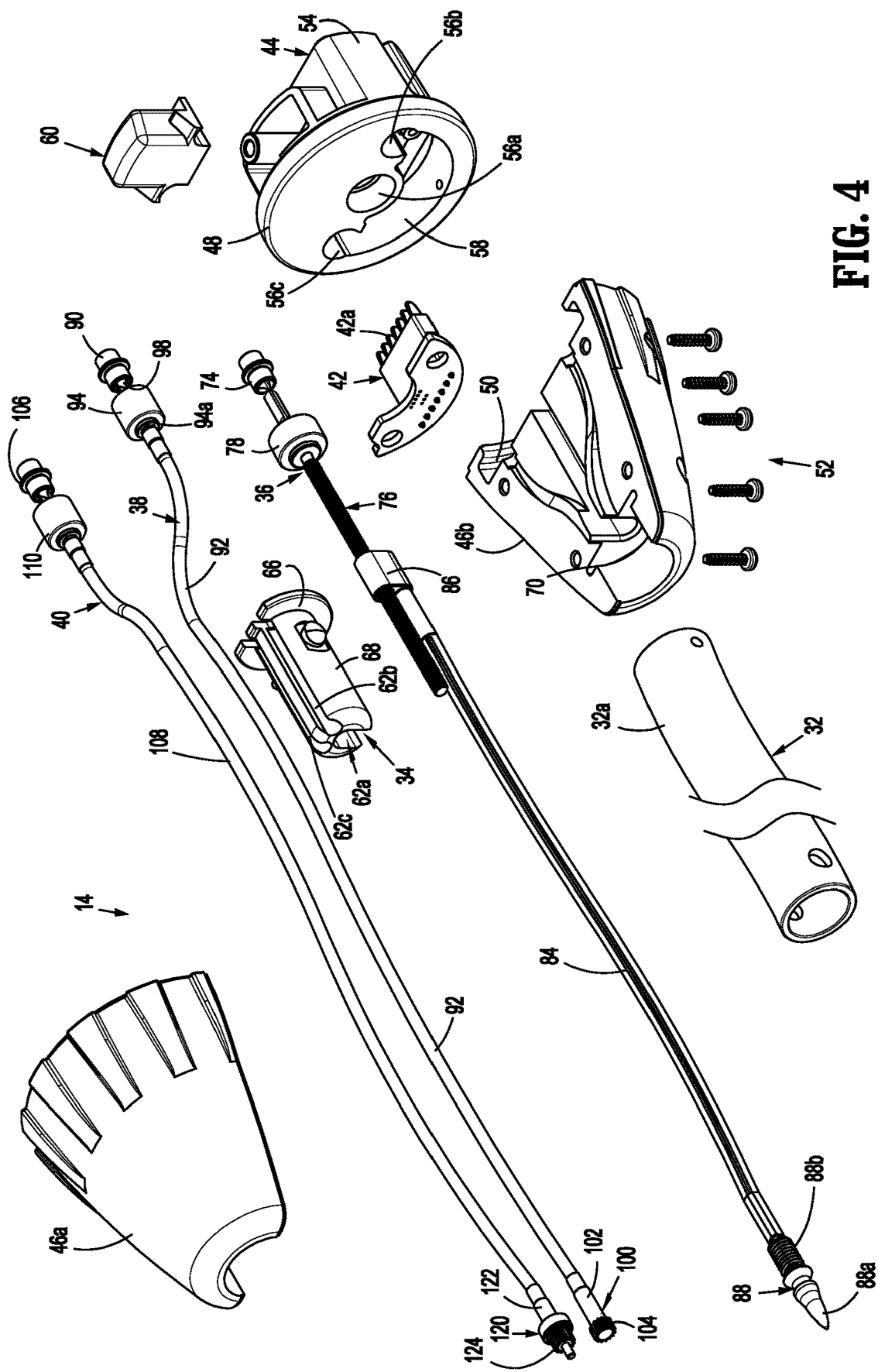
FIG. 4 is an exploded, side perspective view of the adapter assembly of the surgical stapling device shown in FIG. 1.
Figure 5:
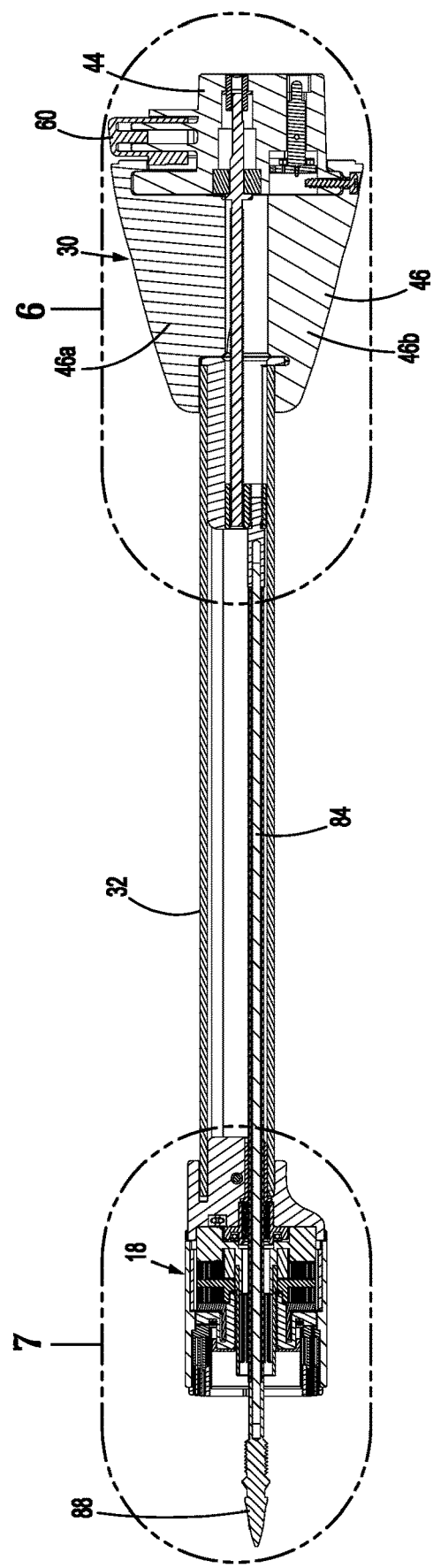
FIG. 5 is a cross-sectional view taken along section line 5-5 of FIG. 2.
Figure 6:
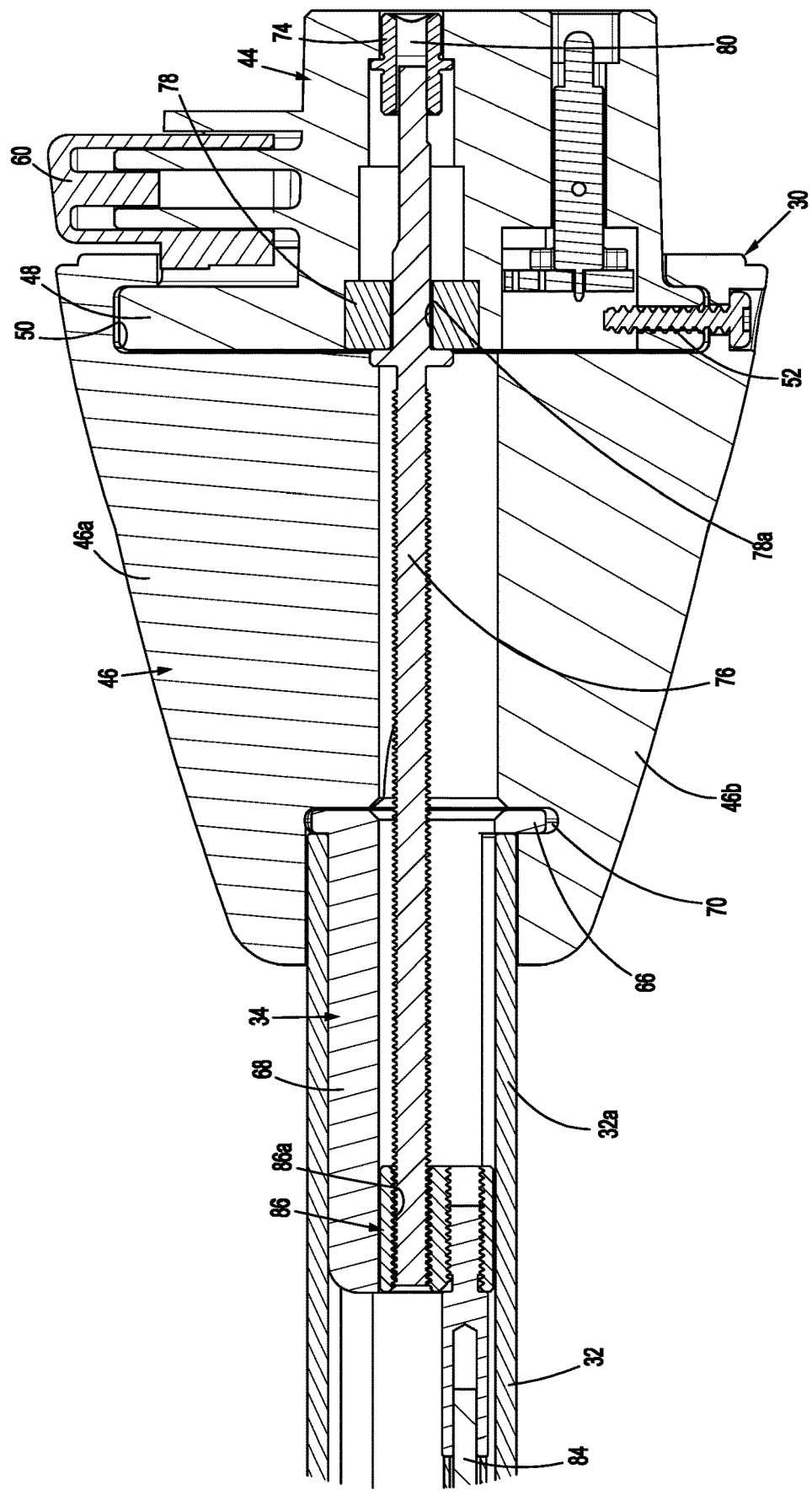
FIG. 6 is an enlarged view of the indicated area of detail shown in FIG. 5.

FIGS. 2-6 illustrate the adapter assembly 14 which includes a proximal housing assembly 30, a flexible outer tube 32, a guide member 34 (FIG. 4), a first drive assembly 36 (FIG. 4), a second drive assembly 38 (FIG. 4), a third drive assembly 40 (FIG. 4), and an electrical coupling member 42 (FIG. 4). The proximal housing assembly 30 includes a hub 44 and a rotation knob 46 that is rotatably supported on the hub 44. In aspects of the disclosure, the hub 44 includes a distal cylindrical portion 48 (FIG. 4) that is received in a cylindrical recess 50 (FIG. 4) defined in a proximal portion of the rotation knob 46 to rotatably couple the rotation knob 46 to the hub 44. In one aspect of the disclosure, the rotation knob 46 is formed from half-sections 46a and 46b that are secured together about the cylindrical portion 48 (FIG. 4) of the hub 44 using, e.g., screws 52 (FIG. 4).

The hub 44 defines through bores 56a, 56b, and 56c (FIG. 4) that receive proximal ends of the first, second, and third drive assemblies 34, 36, and 38 (FIG. 4) of the adapter assembly 14. The hub 44 also defines a cavity 58 (FIG. 4) that receives the electrical coupling member 42. The electrical coupling member 42 is supported within the cavity 58 of the hub 44 and includes proximally extending contacts 42a that are positioned to engage contacts in the handle assembly 12 (FIG. 1) when the adapter assembly 14 is coupled to the handle assembly 12 to electrically couple the control circuitry (not shown) in the handle assembly 12 to sensors (not shown) in the adapter assembly 14 and/or tool assembly 16 to facilitate control of the operation of the stapling device 10 as known in the art. The hub 44 also supports an adapter release button 60 which can be depressed to facilitate separation of the adapter assembly 14 from the handle assembly 12.

The guide member 34 (FIG. 4) includes a body 64 that is fixedly received within a proximal end portion of the 32a (FIG. 6) outer tube 32 and defines first, second, and third guide channels 62a, 62b, and 62c. The body 64 of the guide member 34 includes a proximal flange 66 (FIG. 4) and a cylindrical portion 68 (FIG. 4) that is press fit into the proximal end portion 32a of the outer tube 32 to secure the guide member 34 within the outer tube 32. When the guide member 34 is secured to within the outer tube, the proximal flange 66 is positioned proximally of the outer tube 32 and is received within a circular slot 70 (FIG. 4) defined in the rotation knob 46 to fixedly secure the guide member 34 and the outer tube 32 to the rotation knob 46 of the handle assembly 12.

In one aspect of the disclosure, the first guide channel 62a is substantially U-shaped and receives a proximal portion of the first drive assembly 36, the second guide channel 62b is substantially circular and receives a proximal portion of the second drive assembly 38, and the third guide channel 62c is substantially circular and receives a proximal portion of the third drive assembly 40. The guide member 34 properly positions the drive assemblies 36, 38, and 40 within the flexible outer tube 32 of the adapter assembly 14.

The first drive assembly 36 includes a drive connector 74 (FIG. 6), a threaded drive shaft 76, and a bearing 78. The bearing 78 is received within the through bore 56a (FIG. 6) defined in the hub 44 and defines a through bore 78a (FIG. 6) that receives an unthreaded proximal end portion of the threaded drive shaft 76 such that the threaded drive shaft 76 is rotatably supported within the bearing 78. The drive connector 74 is fixedly secured to the proximal end of the drive screw 76 and defines a recess 80 (FIG. 6) that receives a first drive member (not shown) of the handle assembly 12 (FIG. 1). The drive connector 74 is rotatable to rotate the drive screw 76 within the rotation knob 46.

The drive screw 76 of the first drive assembly 36 is coupled to a flexible approximation link 84 (FIG. 4) by a threaded coupling member 86. The threaded coupling member 86 defines a threaded bore 86a (FIG. 6) that receives the drive screw 76. When the threaded drive screw 76 is rotated within the rotation knob 46 and the outer tube 32, the coupling member 86 translates along the drive screw 76 to move the flexible approximation link 84 within the outer tube 32 between an advanced position (FIG. 6) in which the coupling member 86 is positioned on the distal end of the drive screw 76 and a retracted position in which the coupling member 86 is positioned on a proximal portion of the drive screw 76. The distal end of the flexible approximation link 84 is secured to an anvil retainer 88 that includes a distal trocar portion 88a and a proximal portion 88b. The proximal portion 88b of the anvil retainer 88 is coupled to the flexible approximation link 84 such that the anvil retainer 88 is movable with the flexible approximation link 84 between advanced and retracted positions.

Figure 22:
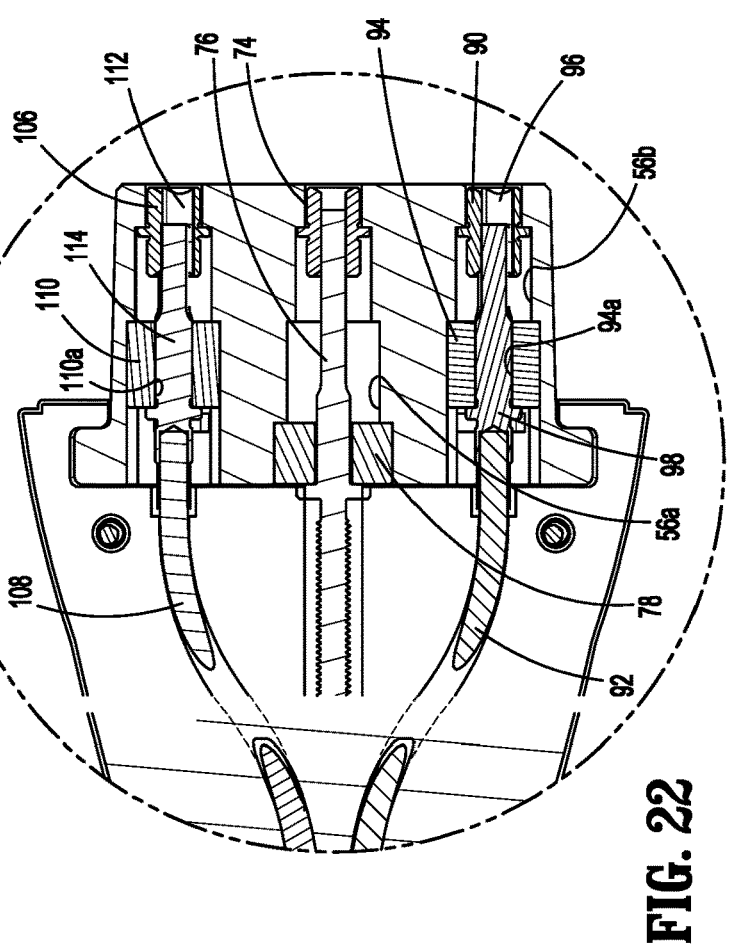
FIG. 22 is an enlarged view of the indicated area of detail shown in FIG. 21.

The second drive assembly 38 (FIG. 4) includes a drive connector 90, a flexible drive shaft 92, and a bearing 94. The bearing 94 is received within the through bore 56b (FIG. 4) defined in the hub 44 and defines a through bore 94a (FIG. 22) that receives proximal end of the flexible drive shaft 92 such that the flexible drive shaft 92 is rotatably supported within the bearing 94. The drive connector 90 is fixedly secured to the proximal end of the flexible drive shaft 92 and defines a recess 96 (FIG. 22) that receives a second drive member (not shown) of the handle assembly 12 (FIG. 1). The drive connector 90 is rotatable to rotate the flexible drive shaft 92 within the rotation knob 46 and outer tube 32. In one aspect of the disclosure, a rigid connector 98 (FIG. 22) is secured to the proximal end of the flexible drive shaft 92 and to the drive connector 90 to translate rotation of the drive connector 90 to corresponding rotation of the flexible drive shaft 92. The rigid drive connector 98 is rotatably supported within the through bore 94a of the bearing 94.

The flexible drive shaft 92 has a distal portion that supports a fire input gear 100 that includes a cylindrical body portion 102 and a distal gear member 104. The fire input gear 100 is fixedly secured to the flexible drive shaft 92 such that rotation of the flexible drive shaft 92 causes corresponding rotation of the fire input gear 100.

The third drive assembly 40 (FIG. 4) includes a drive connector 106, a flexible drive shaft 108, and a bearing 110. The bearing 110 is received within the through bore 56c (FIG. 4) defined in the hub 44 and defines a through bore 110a (FIG. 22) that receives proximal end of the flexible drive shaft 108 such that the flexible drive shaft 108 is rotatably supported within the bearing 110. The drive connector 106 is fixedly secured to the proximal end of the flexible drive shaft 108 and defines a recess 112 (FIG. 22) that receives a third drive member (not shown) of the handle assembly 12 (FIG. 1). The drive connector 106 is rotatable to rotate the flexible drive shaft 108 within the rotation knob 46 and outer tube 32. In one aspect of the disclosure, a rigid connector 114 is secured to the proximal end of the flexible drive shaft 108 and to the drive connector 106 to translate rotation of the drive connector 106 to corresponding rotation of the flexible drive shaft 108. The rigid connector 114 is rotatably supported within the through bore 110a of the bearing 110.

The flexible drive shaft 108 has a distal portion that supports a clamp input gear 120 that includes a cylindrical body portion 122 and a distal gear member 124. The clamp input gear 120 is fixedly secured to the flexible drive shaft 108 such that rotation of the flexible drive shaft 108 causes corresponding rotation of the clamp input gear 120. In aspects of the disclosure, each of the flexible shafts 84, 92, and 108 of the first, second, and third drive assemblies 36, 38, and 40 is enclosed in an outer sheath.

Figure 7:
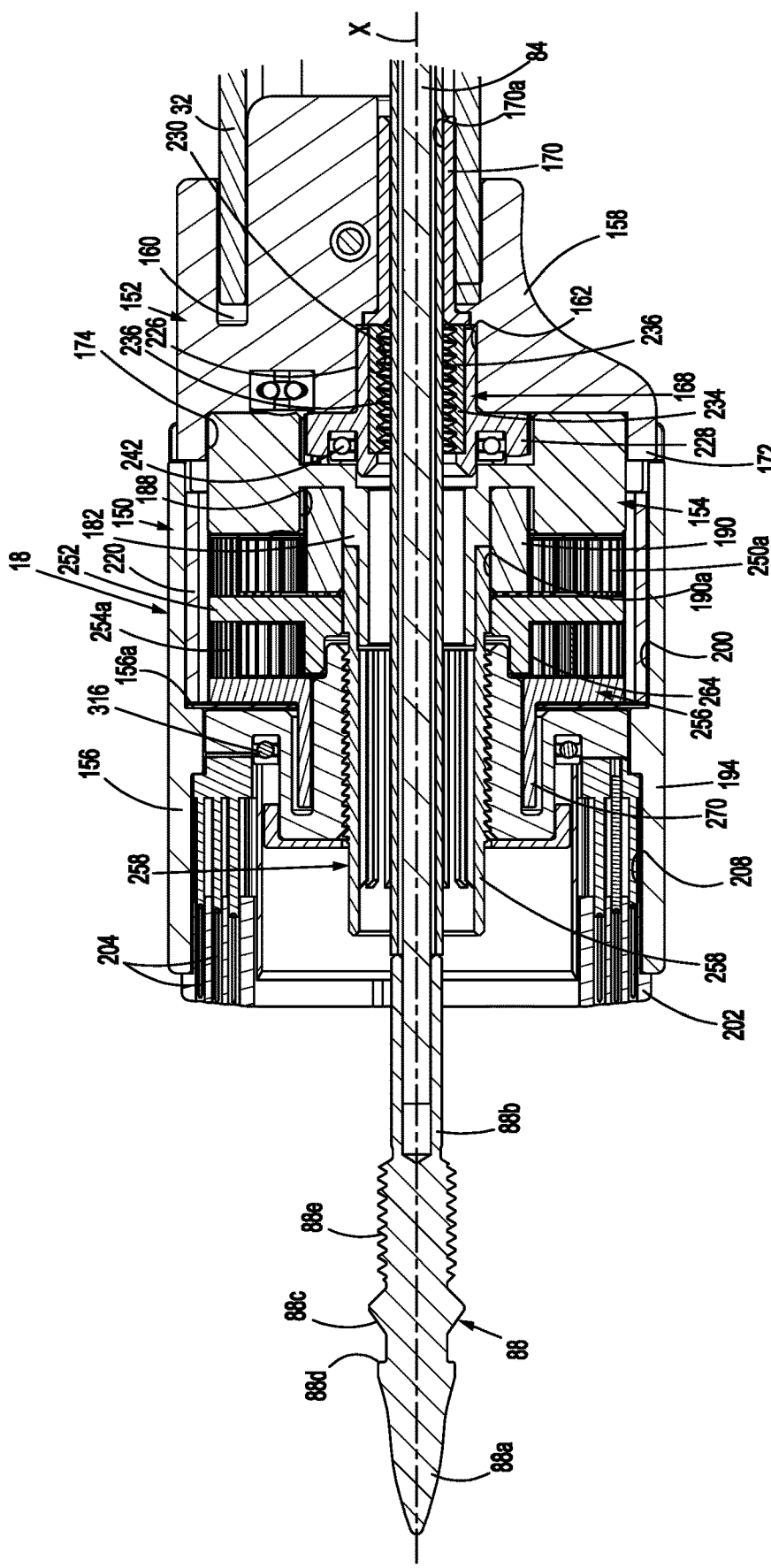
FIG. 7 is an enlarged view of the indicated area of detail shown in FIG. 5.
Figure 8:
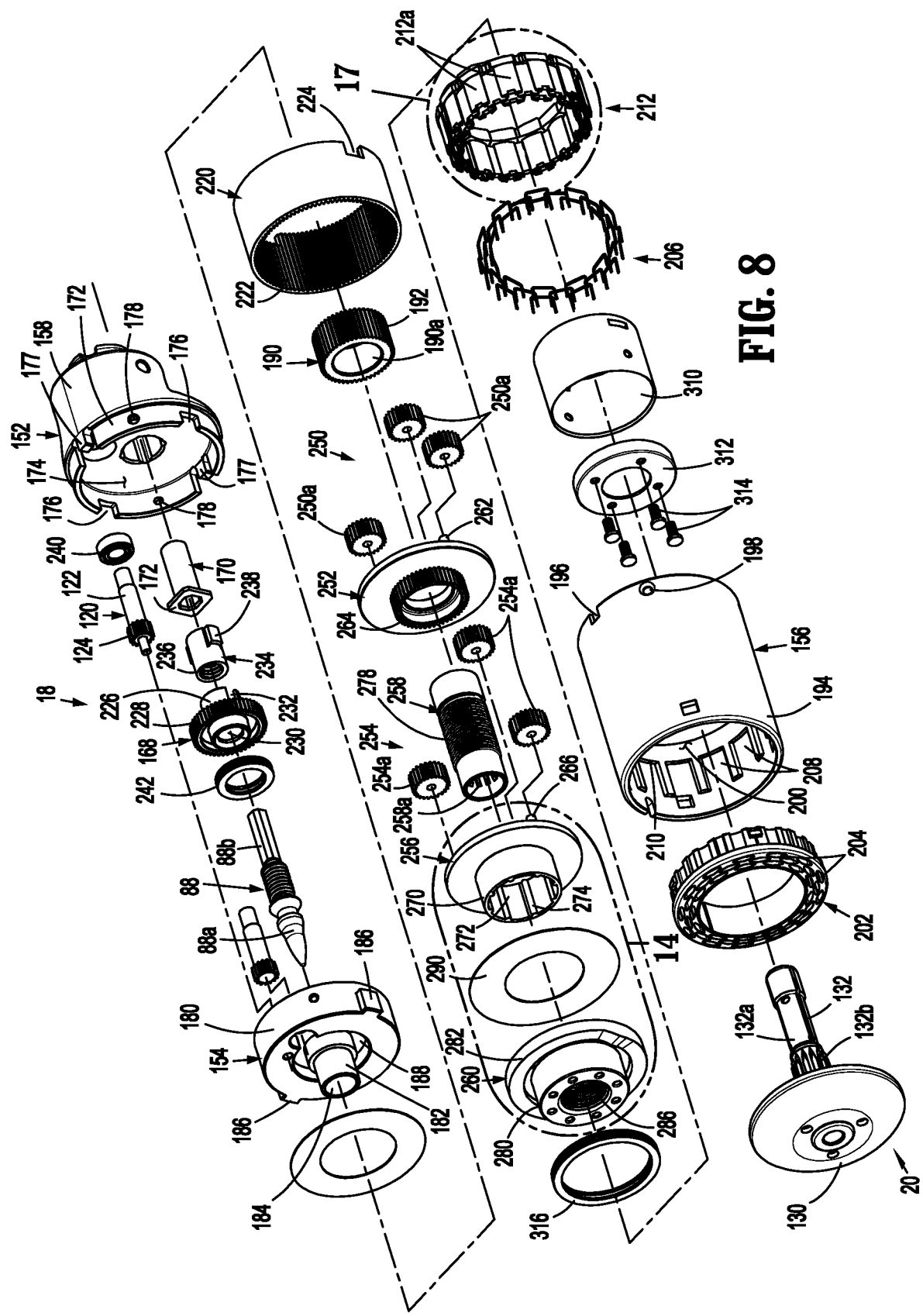
FIG. 8 is an exploded, side perspective view of the tool assembly of the surgical stapling device shown in FIG. 1.
Figure 9:
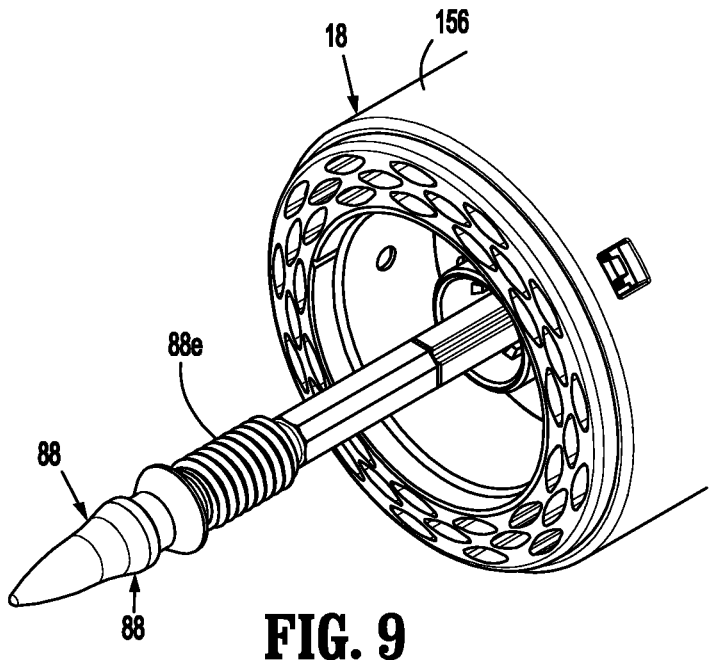
FIG. 9 is an enlarged view of the indicated area of detail shown in FIG. 2.
Figure 10:
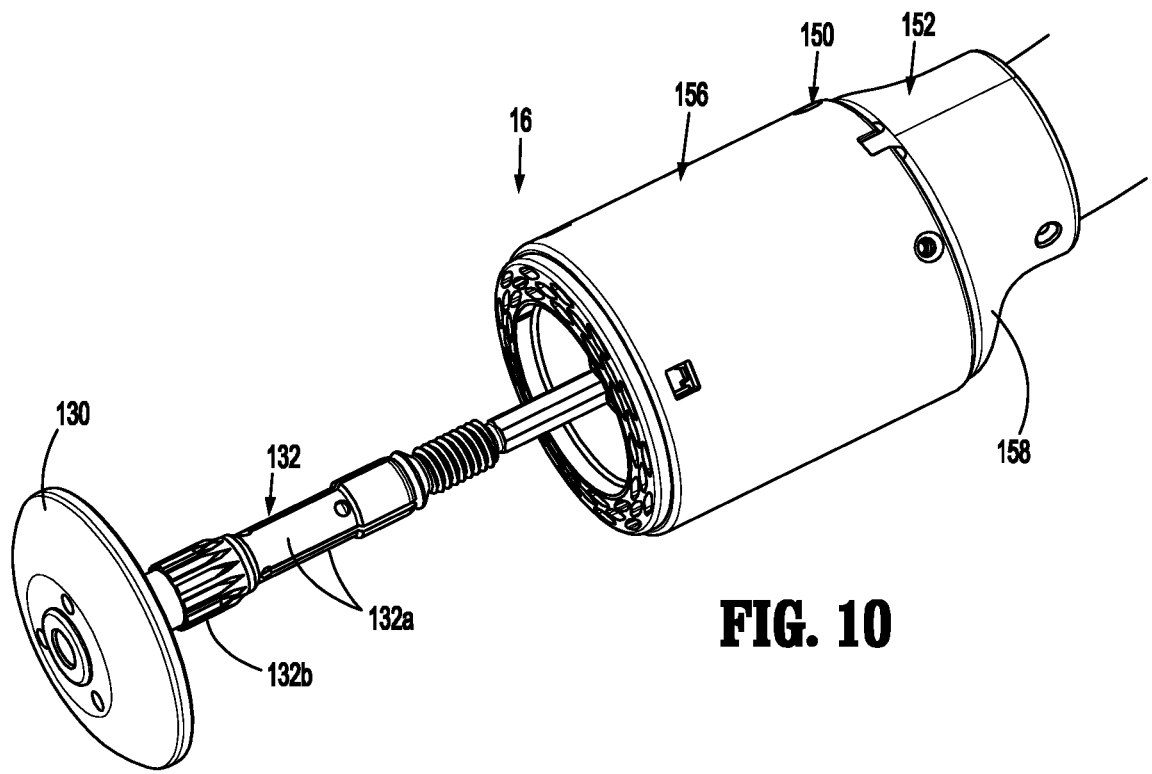
FIG. 10 is an enlarged view of the indicated area of detail shown in FIG. 1.
Figure 11:
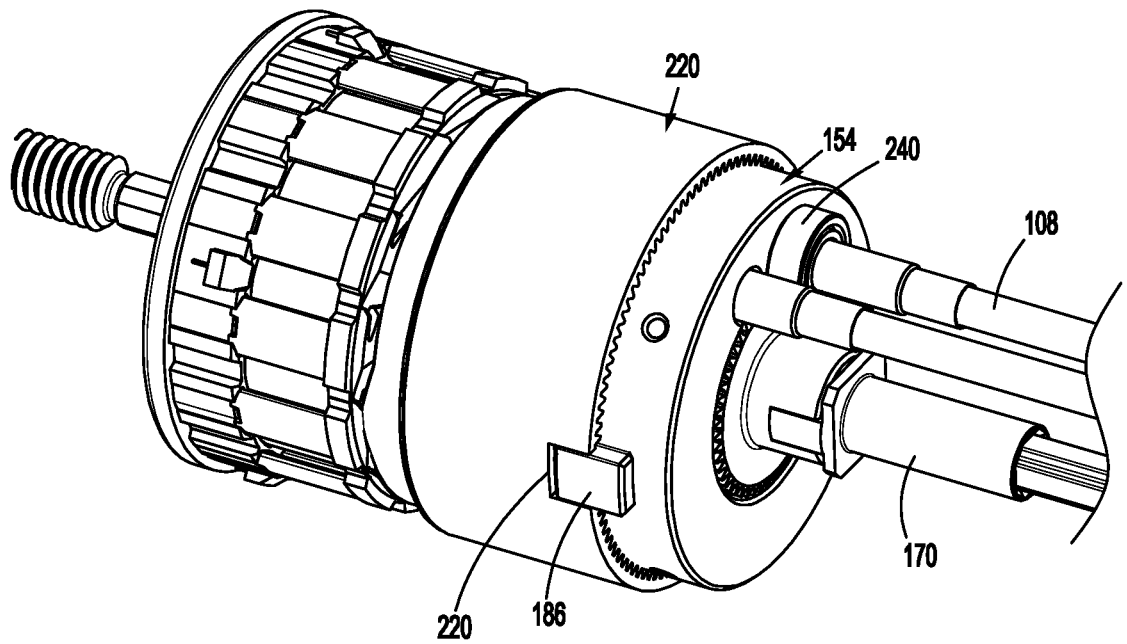
FIG. 11 is a side perspective view of the distal portion of the surgical stapling device shown in FIG. 1 with an outer shell of a shell assembly of the tool assembly removed from the shell assembly.
Figure 12:
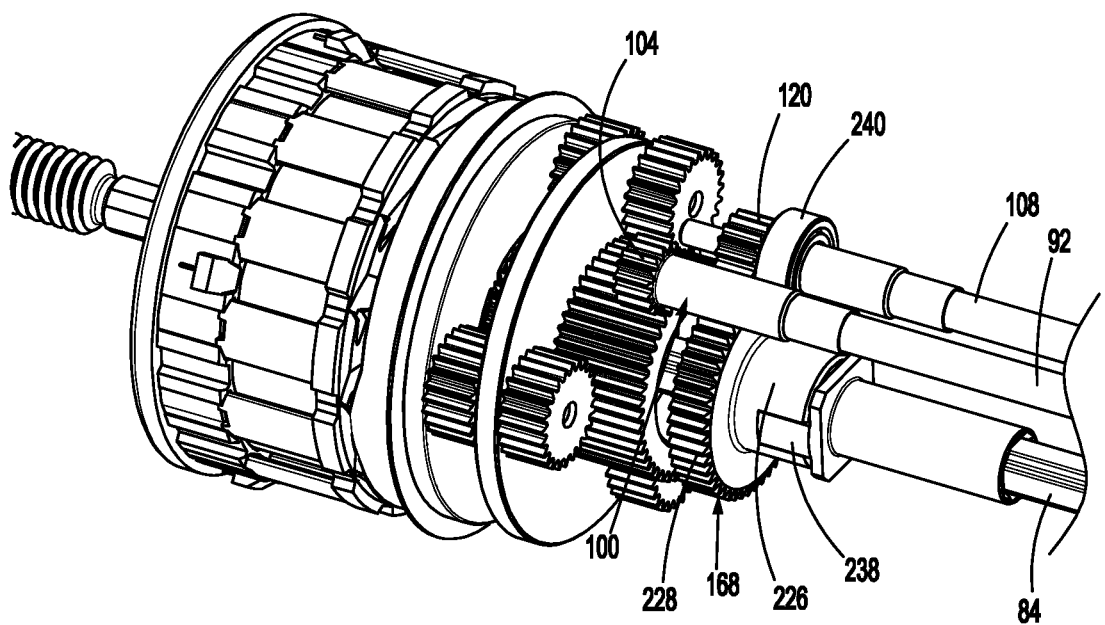
FIG. 12 is a side perspective view of the distal portion of the surgical stapling device shown in FIG. 6 with the outer shell, a ring gear, and a spline tube housing of the shell assembly of the tool assembly removed from the shell assembly.

FIGS. 5-13 illustrate the tool assembly 16 (FIG. 10) of the stapling device 10 which includes the shell assembly 18 and the anvil assembly 20. The anvil assembly 20 includes an anvil head 130 and an anvil shaft 132. The anvil shaft 132 has a distal end that is coupled to the anvil head 130 and a proximal portion that is adapted to be releasably coupled to the anvil retainer 88 (FIG. 8). In aspects of the disclosure, the proximal portion of the anvil shaft 132 includes resilient fingers 132a (FIG. 10) that define a longitudinal cavity (not shown) that receives the anvil retainer 88. When the anvil retainer 88 is inserted into the longitudinal cavity of the anvil shaft 132, the resilient fingers 132a of the anvil shaft 132 engage and move along an outwardly diverging surface 88c (FIG. 7) of the anvil retainer 88 and are deformed outwardly to facilitate passage of the anvil retainer 88 into the longitudinal cavity. When the anvil retainer 88 is received within the longitudinal cavity, the resilient fingers 132a of the anvil shaft 132 return to their nondeformed condition and engage an annular shoulder 88d of the anvil retainer 88 to releasably couple the anvil shaft 132 to the anvil retainer 88 (FIG. 10). The anvil shaft 132 also supports a plurality of longitudinal splines 132b that are spaced about the periphery of the anvil shaft 132. In some aspects of the disclosure, the anvil head 130 is pivotably coupled to the anvil shaft 132. For a more detailed description of an anvil assembly including a pivotable head assembly, see, e.g., U.S. Pat. No. 6,945,444 ("the '444 Patent").

Figures 23, 24:
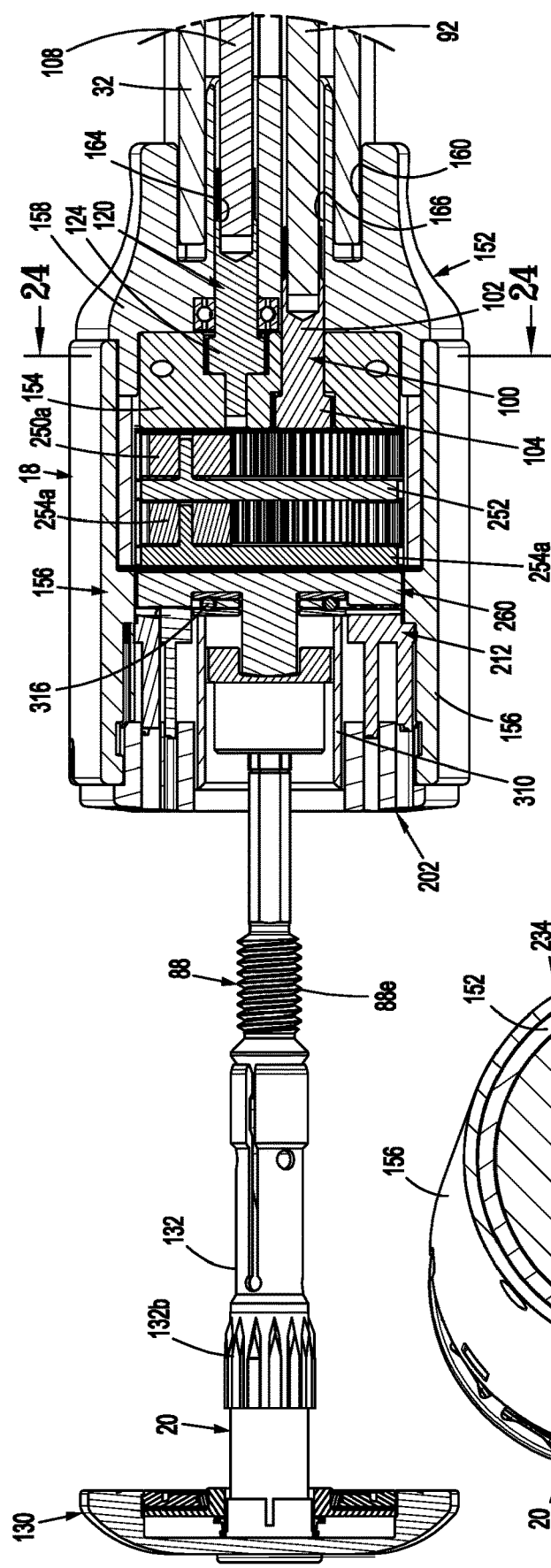
FIG. 23 is an enlarged view of the indicated area of detail shown in FIG. 21.
FIG. 24 is a cross-sectional view taken along section line 24-24 of FIG. 23.

The shell assembly 18 includes housing assembly 150 that includes a proximal housing 152, a spline tube housing 154 (FIG. 8), and a shell housing 156. The proximal housing 152 includes a body 158 having a proximal portion that defines an annular recess 160 (FIG. 7), a first through bore 162 (FIG. 7), a second through bore 164 (FIG. 23), and a third through bore 166 (FIG. 23). The first through bore 162 is centrally located along a longitudinal axis "X" (FIG. 7) of the shell assembly 18 and receives the flexible approximation link 84 of the first drive assembly 36. A distal portion of the first through bore 162 rotatably supports a clamp gear 168 (FIG. 7) and a proximal portion of the first through bore 162 receives a trocar guide 170 (FIG. 7). The trocar guide 170 defines a through bore 170a that slidably receives the flexible approximation link 84. The distal portion of the proximal housing 152 includes an annular extension 172 that defines a cavity 174 (FIG. 7). The annular rim 172 defines cutouts 176 (FIG. 8), tabs 177, and openings 178.

Figure 29:
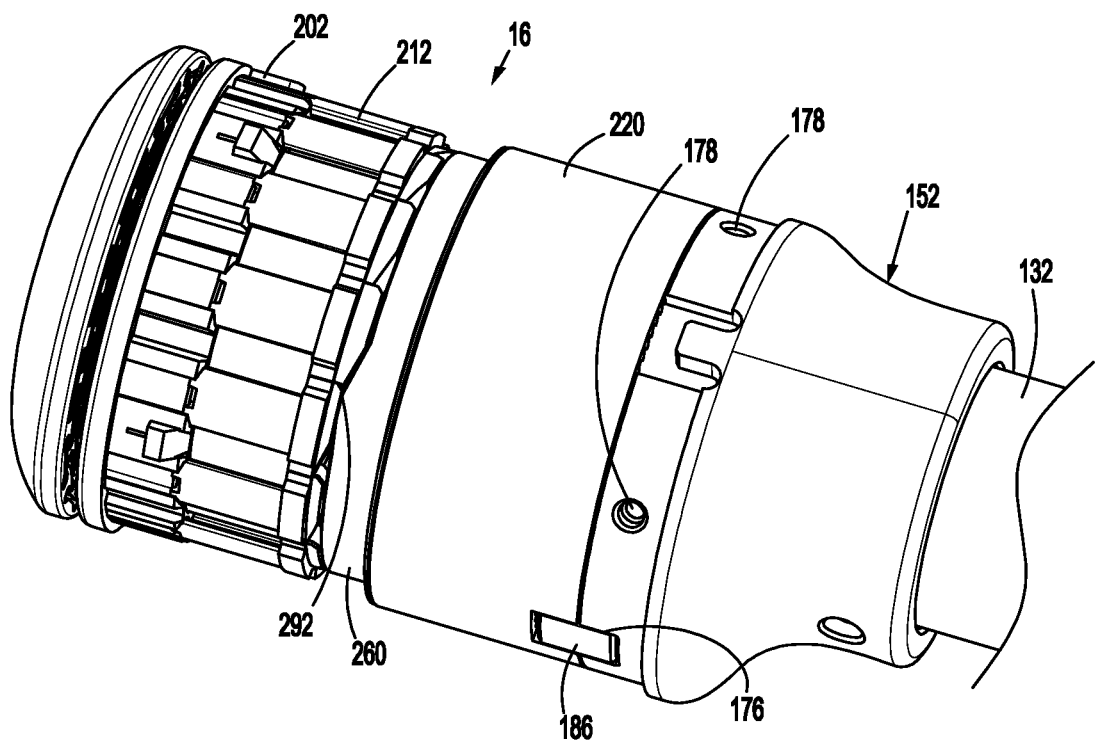
FIG. 29 is a side perspective view of the tool assembly of the surgical stapling device shown FIG. 28 with the shell housing of the shell assembly removed and the tool assembly in the clamped position.
Figure 30:
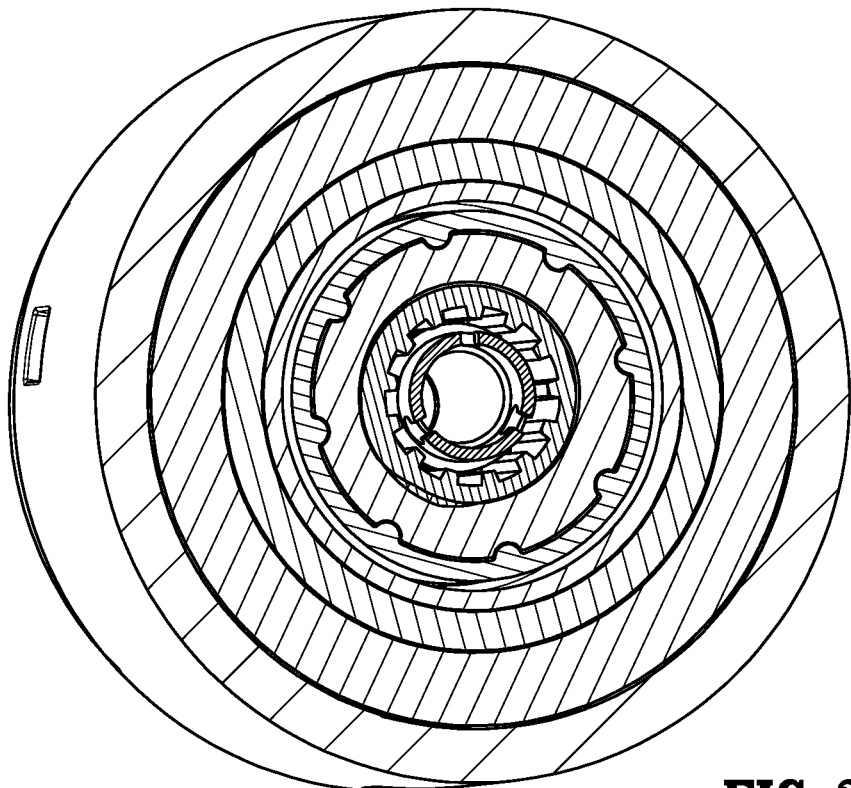
FIG. 30 is a cross-sectional view taken along section line 30-30 of FIG. 28.
Figure 31:
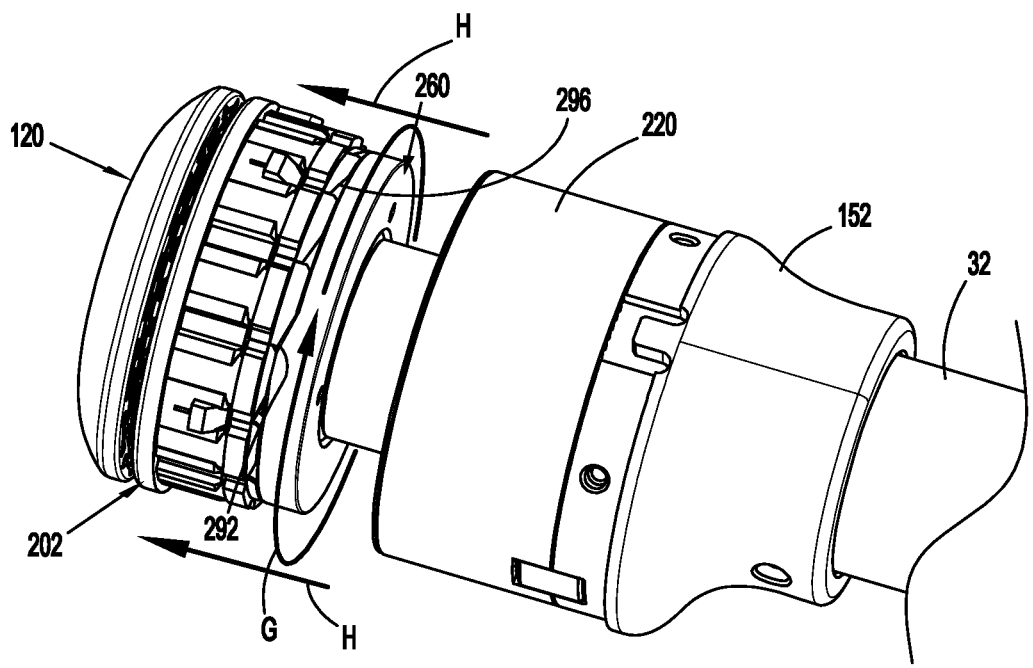
FIG. 31 is a side perspective view of the tool assembly shown in FIG. 29 with the shell housing removed and the stapling device in a fired condition.
Figure 32:
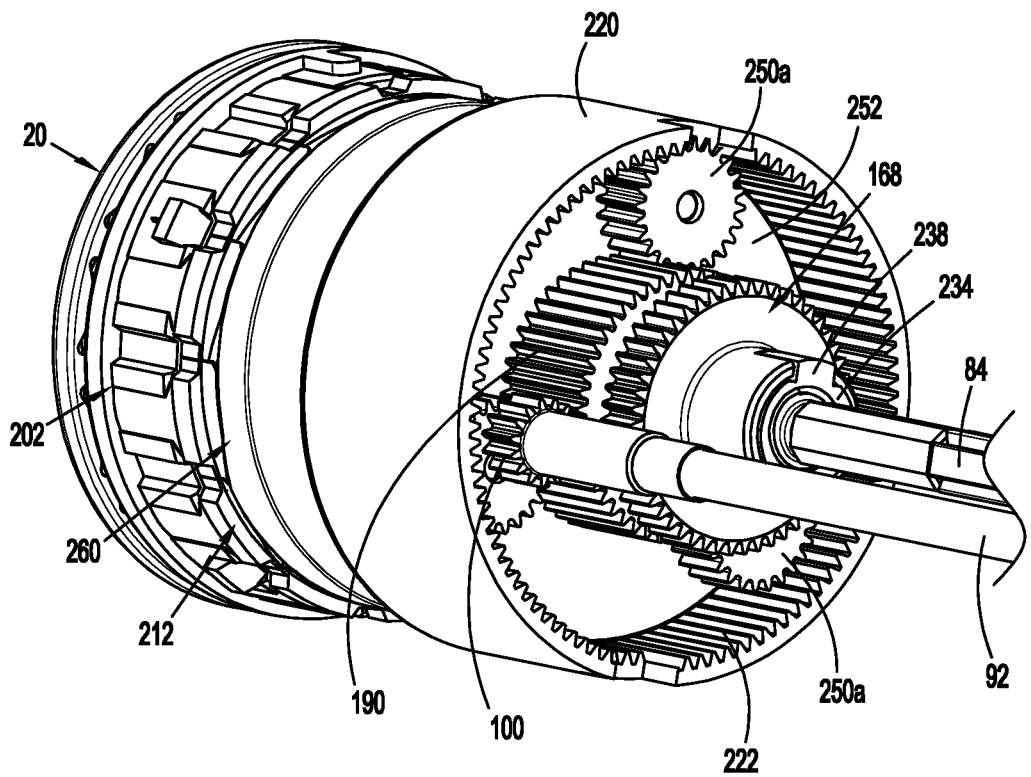
FIG. 32 is a perspective view from the proximal end of the tool assembly shown in FIG. 31 with the stapling device in a fired condition and the shell housing and a tube housing removed.

The spline tube housing 154 (FIG. 8) includes a body 180 that has a circular configuration and includes a small diameter cylindrical extension 182 that extends distally from the body 180 and defines a longitudinal through bore 184 (FIG. 8). The body 180 includes ribs 186 that extend outwardly from an outer periphery of the body 180. The ribs 186 are received within the cutouts 176 (FIG. 29) of the annular rim 172 of the proximal housing 152 to rotatably fix the spline tube housing 154 to the proximal housing 152. The spline tube housing 154 defines an annular recess 188 (FIG. 8) that is positioned between the body 180 and the cylindrical extension 182. A sun gear 190 (FIG. 7) defines a central through bore 190a and is rotatably supported about the cylindrical extension 182 of spline tube housing 154 within the annular recess 188 defined in the spline tube housing 154. The sun gear 190 includes a cylindrical outer surface that has gear teeth 192 (FIG. 8).

The shell housing 156 of the housing assembly 150 includes a cylindrical body 194 (FIG. 8) that has a proximal portion and a distal portion. The proximal portion of the cylindrical body 194 defines cutouts 196 (FIG. 8) and is received about the annular rim 172 (FIG. 8) of the proximal housing 152 such that the tabs 177 (FIG. 8) on the proximal housing 152 are received within the cutouts 196 of the shell housing 156. Receipt of the tabs 177 within the cutouts 196 positions the proximal housing 152 in proper alignment with the shell housing 156 and prevents relative rotation between the housings 152 and 156. The proximal portion of the shell housing 156 and the proximal housing 152 are fixedly secured together using screws (not shown) which are received through openings 198 in the shell housing 156 and the openings 178 in the rim 172 of the proximal housing 152.

The shell housing 156 extends distally from the proximal housing 152 about the spline tube housing 154 and defines an inner cavity 200 (FIG. 8). The distal portion of the shell housing 156 supports an annular staple cartridge 202 that defines staple receiving slots 204. Each of the staple receiving slots 204 (FIG. 8) receives a staple 206. In one aspect of the disclosure, the staple receiving slots 204 are formed in one or more circular rows in the staple cartridge 202, e.g. two or three. In aspects of the disclosure, a distal portion of the shell housing 156 includes an inner surface that defines a plurality of spaced longitudinal channels 208 (FIG. 8) and shoulder 210 that is positioned at a proximal end of each of the longitudinal channels 208. The channels 208 receive and guide pushers 212a (FIG. 8) of a segmented pusher assembly 212 that is supported in the distal portion of the inner cavity 200 of the shell housing 156 adjacent the staple cartridge 202.

The shell assembly 18 includes a ring gear 220 that has internal gear teeth 222 (FIG. 8) and is supported within the cavity 200 of the shell housing 156 proximally of the segmented pusher assembly 212. The ring gear 220 is clamped between a shoulder 156a (FIG. 7) of the shell housing 156 and the proximal body 152 of the housing assembly 150. The ring gear 220 includes cutouts 224 (FIG. 8) that receive the ribs 186 (FIG. 11) on the outer surface of the body 180 of the spline tube housing 154 of the housing assembly 150 to rotatably fix the ring gear 220 within the cavity 200 of the shell housing 156.

The shell assembly 18 includes a close approximation assembly that includes the clamp gear 168 and a clamp nut 234. The clamp gear 168 includes a hub portion 226 and a gear member 228 that is supported about a distal portion of the hub portion 226. The hub portion 226 defines a through bore 230 that receives the flexible approximation link 84. The proximal portion of the hub portion 226 defines a cutout 232 (FIG. 8) and is received within the first through bore 162 (FIG. 7) of the proximal housing 152 such that the clamp gear 168 is rotatably supported within the cavity 200 of the shell housing 156.

The clamp nut 234 is received within the through bore 230 of the hub portion 226 of the clamp gear 168. The clamp nut 234 defines a threaded bore 236 and includes an external rib 238 (FIG. 8) that is received within the cutout 232 of the clamp gear 168. Receipt of the external rib 238 of the clamp nut 234 within the cutout 232 of the clamp gear 168 secures the clamp nut 234 to the clamp gear 168 such that rotation of the clamp gear 168 causes corresponding rotation of the clamp nut 234.

Figure 13:
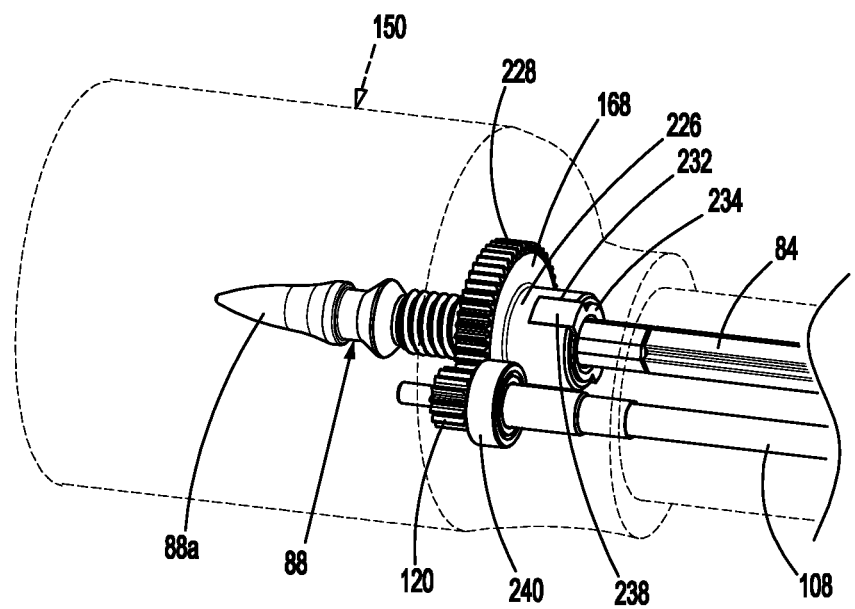
FIG. 13 is a side cross-sectional view of a clamp gear assembly of the tool assembly of the surgical stapling device shown in FIG. 1 with the shell housing shown in phantom.

The clamp input gear 120 is rotatably supported on a bearing 240 (FIG. 11) within the spline tube housing 154 and is engaged with the gear member 228 of the clamp gear 168 (FIG. 13). Rotation of the clamp input gear 120 causes corresponding rotation of the clamp gear 168 and of the clamp nut 234. The flexible approximation link 84 extends through the clamp nut 234. When the flexible approximation link 84 is moved to its retracted position, the anvil retainer 88 is withdrawn partially into the clamp nut 234 such that a threaded outer portion 88e (FIG. 7) of the anvil retainer 88 is received within the threaded bore 236 of the clamp nut 234. When the clamp nut 234 is rotated in this position, the clamp nut 234 retracts the anvil retainer 88 into the clamp nut 234 to effect close approximation of the anvil assembly 20 and the shell assembly 18 as described in detail below. In aspects of the disclosure, a thrust bearing 242 (FIG. 7) is positioned between the clamp gear 168 and the spline tube housing 154.

The shell assembly 18 has a firing mechanism that includes the sun gear 190, a first planetary gear set 250 (FIG. 8), a spider input gear 252, a second planetary gear set 254 (FIG. 8), a spider output gear 256, a threaded spline tube 258, a pusher drive 260, and the segmented pusher 212. The sun gear 190 is rotatably supported within the cavity 200 of the shell housing 156 about the cylindrical extension 182 (FIG. 7) of the spline tube housing 154. The first planetary gear set 250 includes planetary gears 250a. Each of the planetary gears 250a is rotatably supported on a post 262 (FIG. 8) that extends from a proximal face of the spider input gear 252. Although three planetary gears 250a are shown, it is envisioned that one or more planetary gears 250a can be provided. The sun gear 190 is engaged with the planetary gears 250a and the planetary gears 250a are engaged with the internal gear teeth 222 of the ring gear 220. When the sun gear 190 is rotated, the planetary gears 250a rotate within the ring gear 220 to rotate the spider input gear 252 within the cavity 200 of the shell housing 156.

The spider input gear 252 includes distal face and a gear 264 (FIG. 8) that is secured to the distal face. The spider output gear 256 includes proximally extending posts 266. The second planetary gear set 254 includes planetary gears 254a that are rotatably supported on the posts 266 (FIG. 8) that extend from a proximal face of the spider output gear 256. Although three planetary gears 254a are shown, it is envisioned that one or more planetary gears 254a can be provided. The planetary gears 254a are engaged with the gear 264 of the spider input gear 252 and with the internal gear teeth 222 of the ring gear 220 such that rotation of the spider input gear 252 causes the spider output gear 256 to rotate within the cavity 200 of the shell housing 156.

Figure 14:
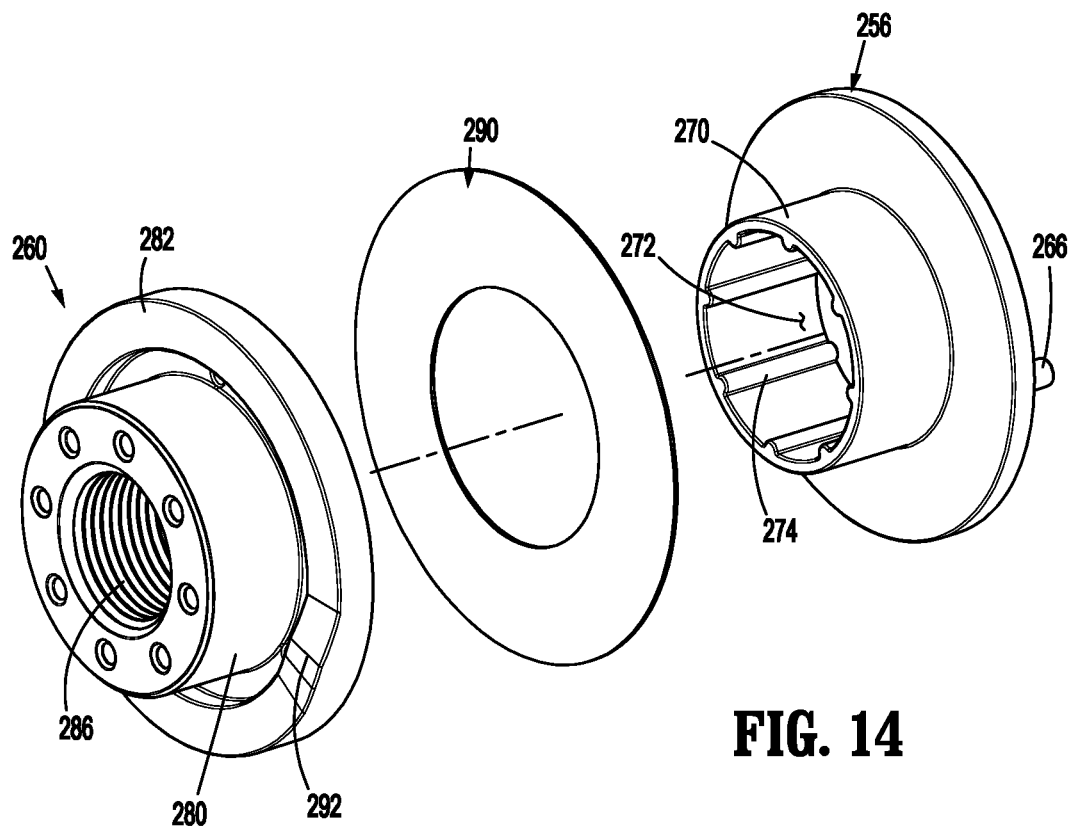
FIG. 14 is an exploded, side perspective view of a firing mechanism of the shell assembly shown in FIG. 29.
Figure 15:
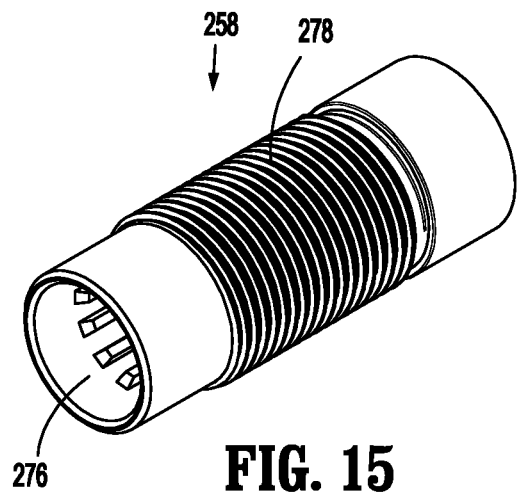
FIG. 15 is a side perspective view of a threaded spline tube of the shell assembly shown in FIG. 29.

The spider output gear 256 is also shown in FIG. 14 and includes a central hub 270 that defines a through bore 272. The central hub 270 of the spider output gear 256 includes an inner surface that includes spaced longitudinally extending ribs 274. The threaded spline tube 258 (FIG. 15) is fixedly secured to the cylindrical extension 182 of the spline tube housing 154 and extends through the through bore 272 of the spider output gear 256. The threaded spline tube 258 defines a through bore 276 and has an outer surface that has threads 278 (FIG. 15) that extend distally of the spider output gear 256. An internal surface of the threaded spline tube 258 includes spaced longitudinally extending splines 258a (FIG. 8) that define channels that receive the splines 132b on the anvil shaft 132 of the anvil assembly 20 to properly orient the anvil assembly 20 in relation to the shell assembly 18 when the tool assembly 16 is moved to its clamped position.

Figure 16:
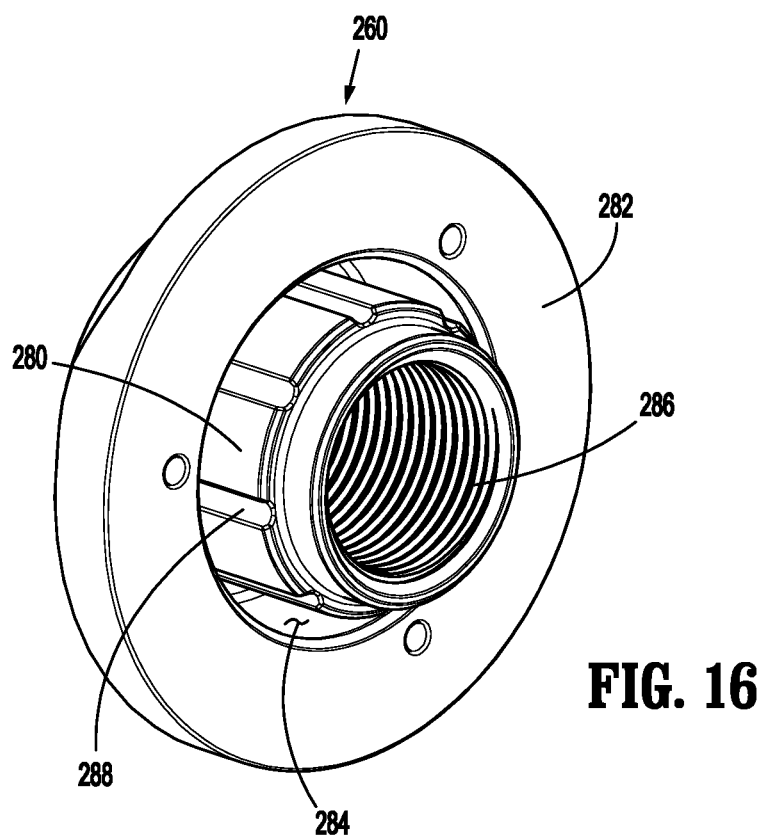
FIG. 16 is side perspective view of the firing mechanism shown in FIG. 14 assembled.

The pusher drive 260 also shown in FIG. 16 includes a central hub 280 and an annular flange 282 that extends radially outwardly from the central hub 280. The central hub 280 of the pusher drive 260 is positioned within the annular flange 282 to define an annular cavity 284 (FIG. 16) that receives the central hub 270 of the spider output gear 256. The central hub 280 of the pusher drive 260 includes an inner threaded surface 286 and an outer surface that defines longitudinal channels 288 (FIG. 16). The threaded surface 286 is engaged with the threads 278 on the outer surface of the spline tube 258 and the longitudinal channels 288 receive the longitudinally extending ribs 274 of the spider output gear 256. Receipt of the longitudinally extending ribs 274 of the spider output gear 256 within the longitudinal channels 288 of the pusher drive 260 couples the spider output gear 256 to the pusher drive 260 such that rotation of the spider output gear 256 causes corresponding rotation of the pusher drive 260. When the pusher drive 260 is rotated, engagement between the inner threaded surface 286 of the pusher drive 260 and the threaded spline tube 258 causes longitudinal movement of the pusher drive 260 along the threaded spline tube 258 to either advance or retract the pusher drive 260 within the shell housing 156. In one aspect of the disclosure, an annular washer 290 is positioned between the spider output gear 256 and the annular flange 282 of the pusher drive 260.

The annular flange 282 of the pusher drive 260 includes a distal face that supports a cam member 292. The cam member 292 projects distally from the annular flange 282 and moves into sequential engagement with the pushers 212a of the segmented pusher assembly 212 as the pusher drive 260 is rotated to advance the pushers 212a from retracted positions to advanced positions to eject the staples 206 from the staple cartridge 202 as described in further detail below.

Figure 17:
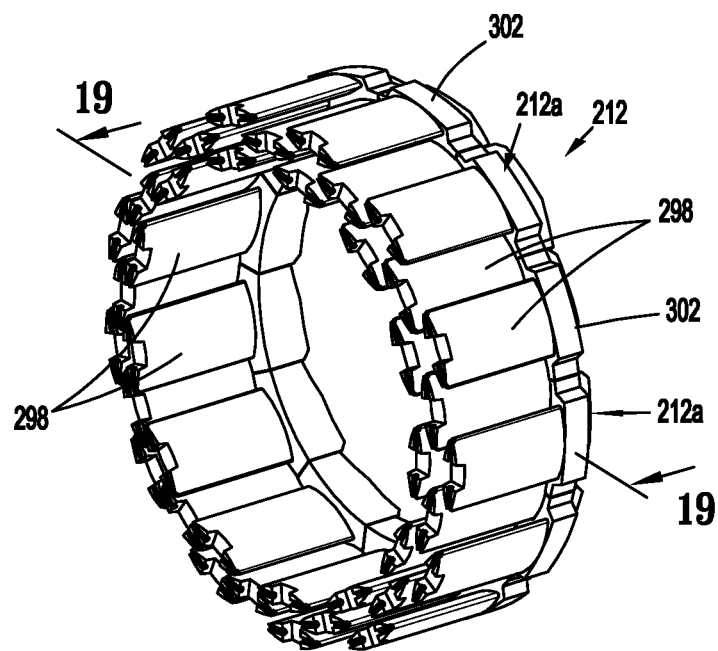
FIG. 17 is an enlarged view of the indicated area of detail shown in FIG. 8.
Figure 18:
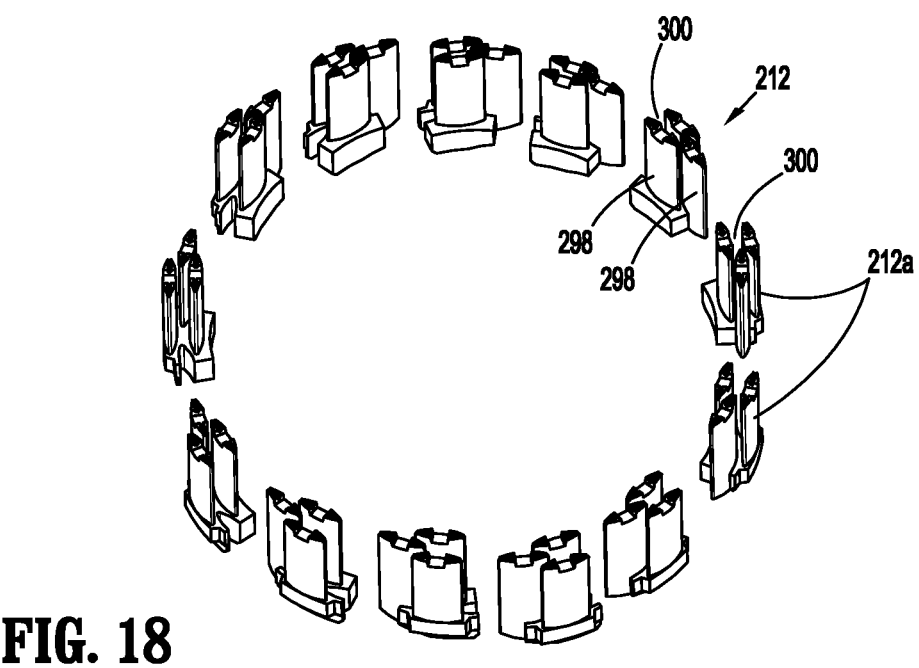
FIG. 18 is an exploded view of the segmented pusher assembly shown in FIG. 17.
Figure 19:
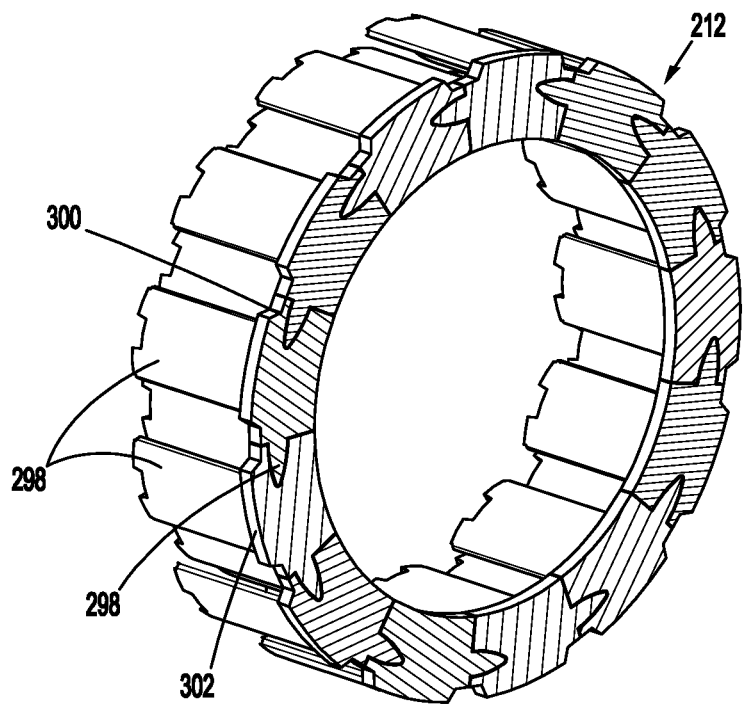
FIG. 19 is a cross-sectional view of a segmented pusher assembly taken along section line 19-19 of FIG. 17.
Figure 20:
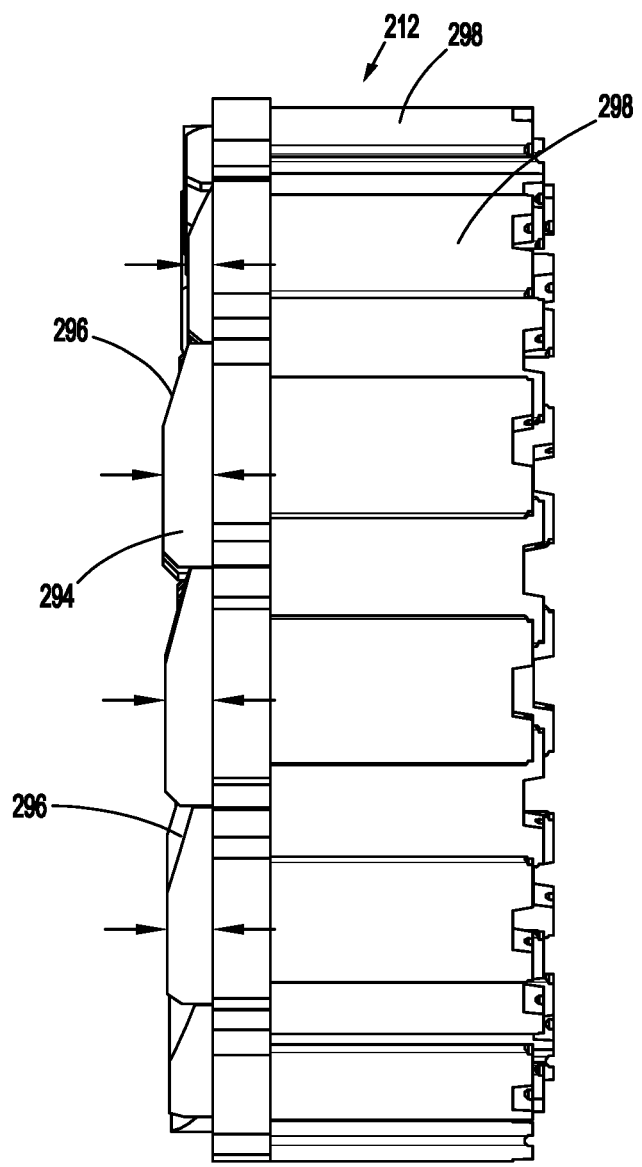
FIG. 20 is a side view of the segmented pusher assembly shown in FIG. 17.
Figure 21:
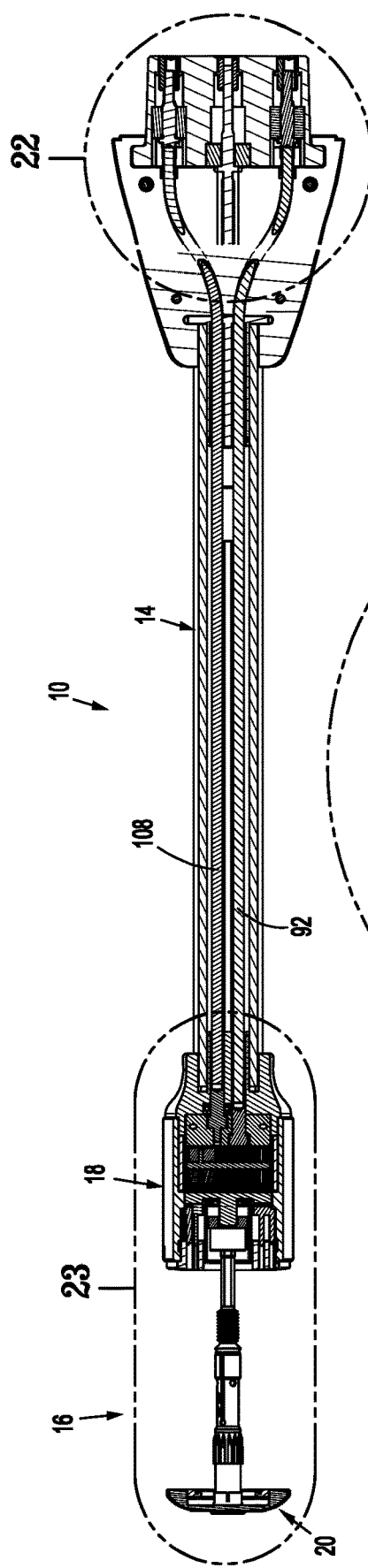
FIG. 21 is a cross-sectional view taken along section line 21-21 of FIG. 3 with the tool assembly in an unclamped position.

FIGS. 17-19 illustrate the segmented pusher assembly 212 which includes a plurality of pushers 212a that are coupled together to form an annular configuration. Each of the pushers 212a (FIG. 25A) has a body 294 that has a proximally facing angled cam surface 296 and fingers 298 that extend distally from the body 294 into the staple receiving slots 204 (FIG. 8) of the staple cartridge 202. In aspects of the disclosure, each of the pushers 212a includes three fingers 298. Two of the fingers 298 are radially aligned with each other to define a recess 300 (FIG. 25A) and the other finger 298 is radially offset from the two radially aligned fingers 294. When the segmented pusher assembly 212 is assembled, each radially offset finger 294 is received in the recess 300 defined by the radially aligned fingers 294 of an adjacent one of the pushers 212 such that the pushers 212a define the annular segmented pusher assembly 212 (FIG. 24).

The body 294 of each of the pushers 212 includes a projection 302 that is received within one of the longitudinal channels 208 (FIG. 8) defined along the interior surface of the shell housing 156. Receipt of the projections 302 within the longitudinal channels 208 of the shell housing 156 guides the pushers 212a the segmented pusher assembly 212 as the pushers 212a move between their advanced and retracted positions.

The shell assembly 18 (FIG. 8) includes an annular knife 310 that is received about the central hub 280 of the pusher drive 260. An annular snap ring 312 is secured to the central hub 280 of the pusher drive 260 and engages an inner surface of the annular knife 310 (FIG. 7) to secure the annular knife 310 to the pusher drive 260. The annular snap ring 312 is secured to the central hub 280 of the pusher drive 260 by screws 314 (FIG. 8). Alternately, the annular snap ring 312 can be press fit onto the central hub 280 of the pusher drive 260. In aspects of the disclosure, a thrust bearing 316 is positioned between the pusher drive 260 and the proximal end of the annular knife 310.

FIGS. 6, and 21-24 illustrate the stapling device 10 in a pre-fired position with the anvil assembly 20 coupled to the anvil retainer 88 and the tool assembly 16 in the open position. In this position, a distal end of the threaded drive shaft 76 (FIG. 6) of the first drive assembly 36 is received in the threaded coupling member 86 and the flexible approximation link 84 of the first drive assembly 36 is in its advanced position such the anvil assembly 20 is spaced from the staple cartridge 202 of the shell assembly 18. In addition, the pusher drive 260, the segmented pusher assembly 212, and the annular knife 310 are in their retracted positions within the shell housing 156 of the shell assembly 18.

Figure 27:
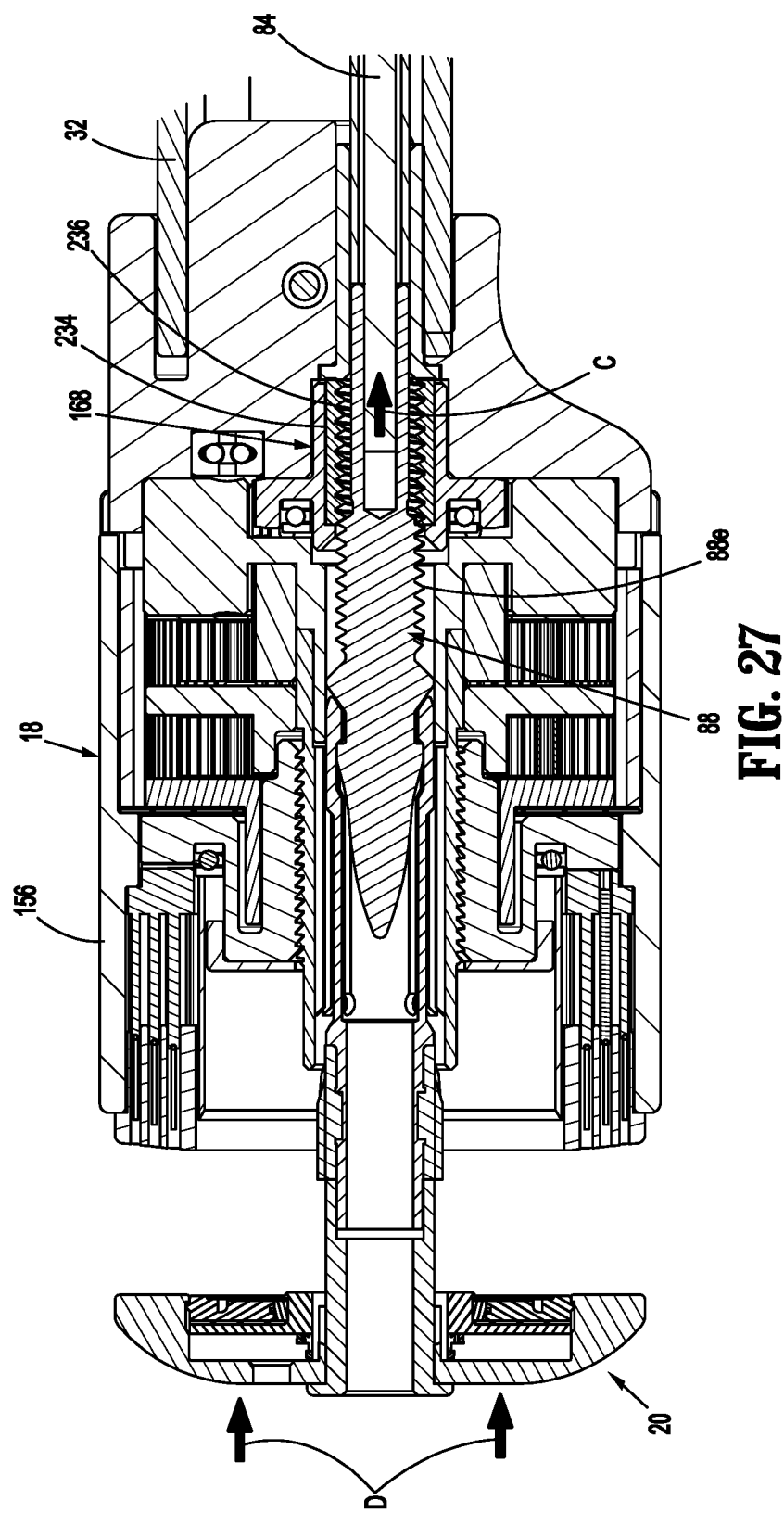
FIG. 27 is an enlarged view of the indicated area of detail shown in FIG. 25.
Figure 28:
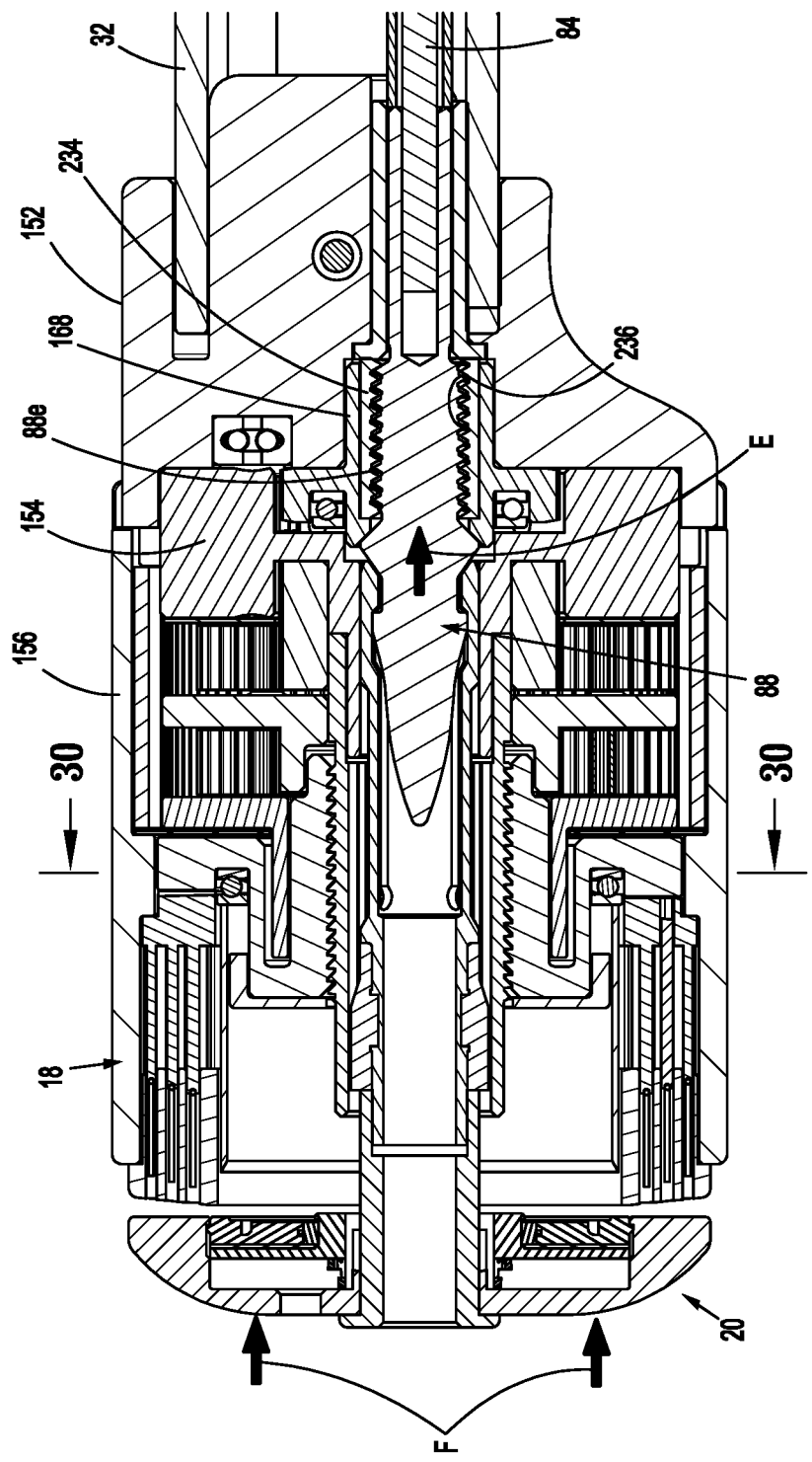
FIG. 28 is a cross-sectional view taken through the tool assembly as the tool assembly moves to the clamped position.

FIGS. 25-27 illustrate the stapling device 10 as the stapling device 10 is actuated to move the tool assembly 16 through a first clamping stage to a partially clamped position. When the handle assembly 12 (FIG. 1) is actuated to activate the first drive assembly 36 (FIG. 4), the threaded drive shaft 76 is rotated in the direction indicated by arrow "A" in FIG. 25 to retract the threaded coupling member 86 within the guide member 34 in the proximal portion of the flexible outer tube 32 of the adapter assembly 14 in the direction indicated by arrow "B" from an advanced position to a retracted position. The threaded coupling member 86 is fixedly coupled to the proximal portion of the flexible articulation link 84. As the threaded coupling member 86 moves from its advanced position towards its retracted position, the flexible articulation link 84 moves within the flexible outer tube 32 of the adapter assembly 14 in the direction of arrow "C" in FIG. 26 from its advanced position towards its retracted position. As described above, the anvil retainer 88 is secured to the distal portion of the flexible articulation link 84 and the anvil assembly 20 is releasably coupled to the anvil retainer 88 such that movement of the flexible articulation link 84 from its advanced position towards its retracted position moves the anvil retainer 88 and thus, the anvil assembly 20 from their advanced positions towards their retracted positions in the direction of arrows "D" in FIG. 27 to position the tool assembly 16 in a partially clamped position in which the anvil head 130 of the anvil assembly 20 is moved closer to the staple cartridge 202 of the shell assembly 18. In the partially clamped position of the tool assembly 16, the threaded outer portion 88e of the anvil retainer 88 enters the threaded bore 236 of the clamp nut 234. The adapter assembly 18 including the flexible outer tube 32 is subjected to minimal compressive forces during this first clamping stage because tissue (not shown) positioned between the anvil head 130 and the staple cartridge 202 is not fully compressed.

FIGS. 13 and 28-30 illustrate the stapling device 10 as the stapling device 10 is actuated to move the tool assembly 16 through a second clamping stage to a fully clamped position. When the handle assembly 12 is actuated to activate the third drive assembly 40, the drive connector 106 is rotated within the hub 44 of the adapter assembly 14 to rotate the clamp input gear 120 (FIG. 13). The clamp input gear 120 is engaged with the gear member 228 of the clamp gear 168 such that rotation of the clamp input gear 120 causes rotation of the clamp gear 168. The clamp nut 234 is fixedly secured within the clamp gear 168 and rotates with the clamp gear 168. When the clamp nut 134 rotates, engagement between the threaded outer portion 88e of the anvil retainer 88 and the threaded bore of the 236 of the clamp nut 234 causes the anvil retainer 88 to move into the clamp nut 234 in the direction indicated by arrow "E" in FIG. 28. As described above, the anvil retainer is coupled to the anvil assembly 18 such that the anvil assembly 20 moves in the direction of arrow "F" in FIG. 28 into close approximation with the staple cartridge 202 of the shell assembly 18 to move the tool assembly 16 to its fully clamped position. The clamping forces to move the tool assembly 16 from the partially clamped position to the fully clamped position during the second clamping stage are contained within the housing assembly 150 of the shell assembly 18 and are not distributed through flexible outer tube 32 of the adapter assembly 14.

Figure 18A:
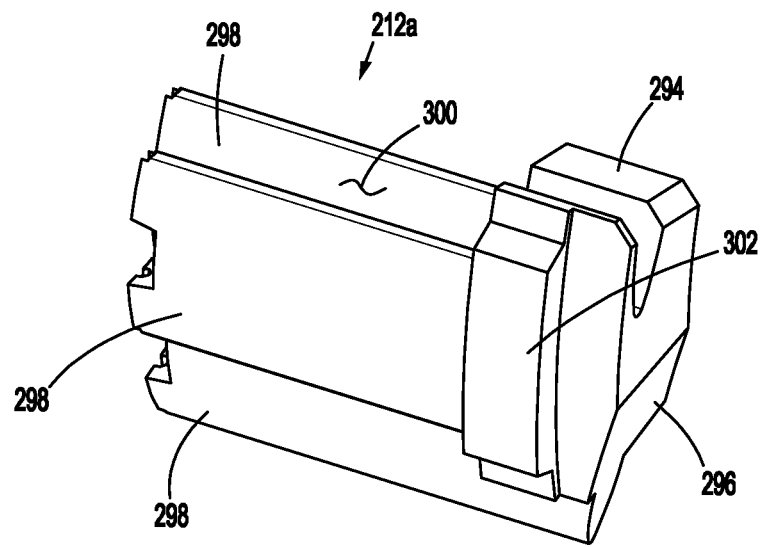
FIG. 18A is a side perspective view of a pusher of the segmented pusher assembly shown in FIG. 17.
Figure 33:
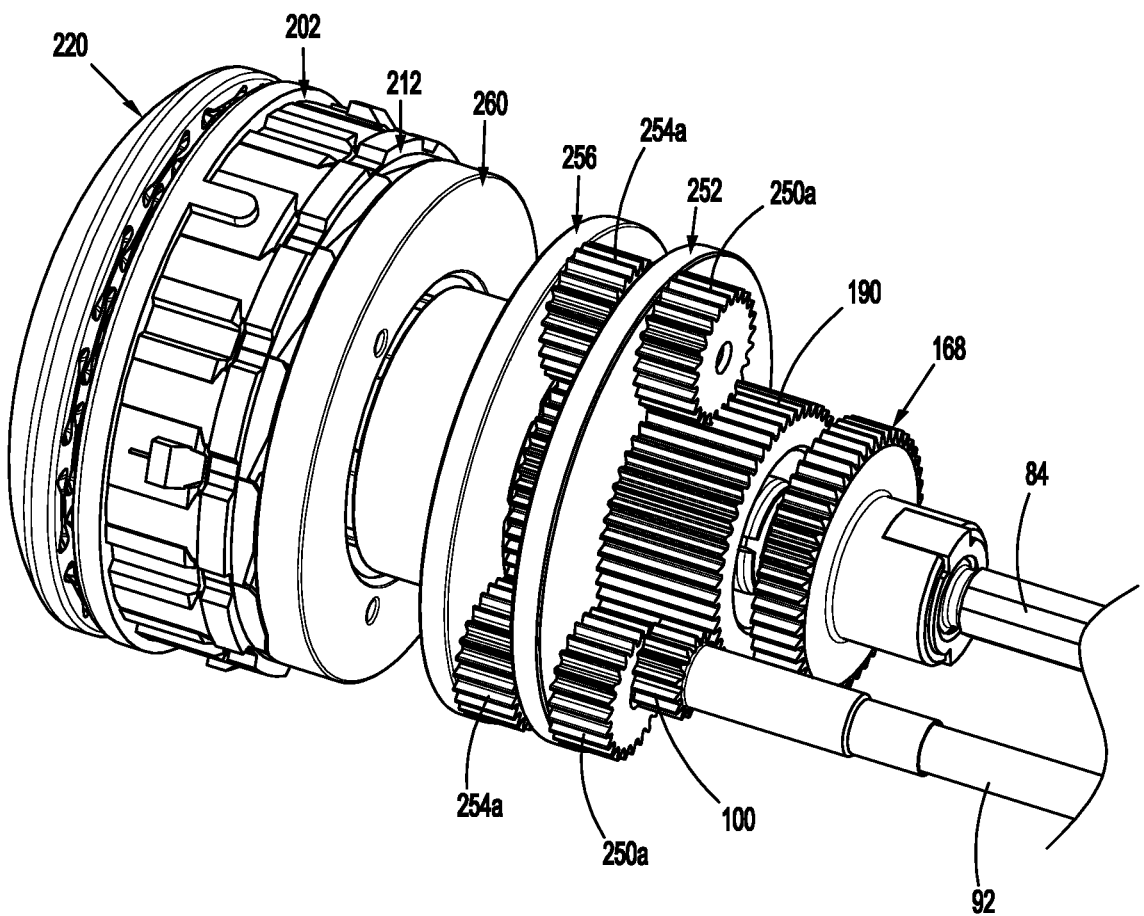
FIG. 33 is a side view of the tool assembly shown in FIG. 32 with the ring gear also removed.

FIGS. 20 and 31-34 illustrate the stapling device 10 (FIG. 1) as the stapling device 10 is fired. In order to fire staples 206 (FIG. 8) from the staple cartridge 202 of the stapling device 10, the handle assembly 12 is actuated to activate the second drive assembly 38 (FIG. 4). When the handle assembly 12 is actuated to activate the second drive assembly 38 (FIG. 4), the drive connector 90 is rotated within the hub 44 of the adapter assembly 14 to rotate the flexible drive shaft 92 and the fire input gear 100 (FIG. 33). As described above, the fire input gear 100 is coupled to the pusher drive 260 by the sun gear 190, the first planetary gear set 250 (FIG. 8), the spider input gear 252, the second planetary gear set 254 (FIG. 8), and the spider output gear 256 such that rotation of the fire input gear 100 causes rotation of the pusher drive 260 about the threaded spline tube 258. As the pusher tube 260 rotates about the threaded spline tube 258 in the direction indicated by arrow "G" in FIG. 31, the pusher drive 260 also moves longitudinally in the direction of arrows "H" in FIG. 31 towards its advanced position. As the pusher drive 260 rotates within the shell housing 156, the cam member 292 on the pusher drive 260 sequentially engages the angled cam surfaces 296 (FIG. 18A) on each of the pushers 212a to advance the pushers 212a. As the pushers 212a are advanced, the fingers 298 on each of the pushers 212a are advanced through the staple receiving slots 204 of the staple cartridge 202 to eject the staples 206 from the staple cartridge 202. In order to compensate for the longitudinal advancement of the pusher drive 260 about the threaded spline tube 258, the angled cam surfaces 296 of the pushers 212a of the segmented pusher 212 are longitudinally offset from each other in stepped fashion to compensate for longitudinal movement of the pusher drive 260. More specifically, the angled cam surface 296 of first pusher 212a to be engaged by the pusher drive 260 is positioned further proximally than the angled cam surfaces 296 of the second and subsequent pushers 212a of the segmented pusher 212 such that the effective stroke length of each of the pushers 212a caused by rotation and longitudinal advancement of the pusher drive 260 is the same. By providing the same stroke length to each of the pushers 212a, proper staple formation of each of the staples 206 can be achieved. It is envisioned that the staples 206 (FIG. 8) can be formed by rotating the pusher drive 260 through one or more revolutions, e.g., two, three etc. The disclosed pusher drive 260 which is rotated through one or more revolutions to sequentially eject the staples 206 from the staple cartridge 202 of the shell assembly 18 minimizes the firing forces required to fire the stapling device 10 and also confines the firing forces within the housing assembly 30 of the shell assembly 18.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A shell assembly comprising:
  a shell housing defining a cavity, a staple cartridge supported on the shell housing, a segmented pusher assembly, and a pusher drive movable in a longitudinal direction, the staple cartridge defining staple receiving slots that receive staples, the segmented pusher assembly positioned within the cavity of the shell housing and including a plurality of pushers arranged in an annular configuration, each of the pushers including an angled cam surface and being movable independently of other pushers of the plurality of pushers from a retracted position to an advanced position, with the cam surfaces of the plurality of pushers being longitudinally offset from each other in stepped fashion to compensate for longitudinal movement of the pusher drive, the pusher drive supported within the cavity of the shell housing and including a cam member, the pusher drive being rotatable to move the cam member into sequential engagement with the cam surfaces of the plurality of pushers of the segmented pusher to sequentially advance the plurality of pushers of the segmented pusher from their retracted positions to their advanced positions to eject the staples from the staple cartridge.

2. The shell assembly of claim 1, further including a threaded spline tube secured within the shell housing, the pusher drive rotatably positioned about the threaded spline tube.

3. The shell assembly of claim 2, wherein the pusher drive includes a central hub that includes an inner threaded surface and the threaded spline tube has an outer surface that includes threads, the threads on the outer surface of the threaded spline tube being engaged with the inner threaded surface of the pusher drive such that rotation of the pusher drive about the threaded spline tube causes longitudinal movement of the pusher drive about the threaded spline tube.

4. The shell assembly of claim 3, further including a sun gear, a first planetary gear set, a spider input gear, a second planetary gear set, and a spider output gear, the first planetary gear set rotatably supported on the spider input gear, the second planetary gear set supported on the spider output gear, and the sun gear is engaged with the first planetary gear set, wherein rotation of the sun gear causes rotation of the spider output gear.

5. The shell assembly of claim 4, wherein the shell assembly includes a ring gear that is fixedly secured to the shell housing, the ring gear being engaged with the first and second planetary gear sets such that rotation of the first planetary gear set causes rotation of the spider input gear and rotation of the second planetary gear set causes rotation of the spider output gear.

6. The shell assembly of claim 5, wherein the pusher drive is rotatably fixed to the spider output gear.

7. The shell assembly of claim 6, wherein the spider output gear includes a central hub that defines a through bore, the central hub of the spider output gear having an inner surface that includes longitudinally extending ribs.

8. The shell assembly of claim 7, wherein the central hub of the pusher drive defines longitudinally channels that receive the longitudinally extending ribs of the central hub of the spider output gear to rotatably fix the spider output gear to the pusher drive.

9. A surgical stapling device comprising:
an adapter assembly including:
a flexible outer tube having a proximal portion and a distal portion;
a first drive assembly extending through the flexible outer tube, the first drive assembly including a flexible approximation link having a proximal portion and a distal portion and an anvil retainer secured to the distal portion of the flexible articulation link, the anvil retainer including a threaded outer portion; and
a second drive assembly extending through the flexible outer tube, the second drive assembly including a flexible drive shaft having a proximal portion and a distal portion, and an input gear secured to the distal portion of the flexible drive shaft;
a tool assembly secured to the distal portion of the flexible outer tube, the tool assembly including:
an anvil assembly including an anvil head and an anvil shaft secured to the anvil head;
a shell assembly including a housing and a clamp gear supported within the housing of the shell assembly, the clamp gear engaged with the input gear of the second drive assembly;
wherein activation of the first drive assembly through a first clamping stage retracts the flexible approximation link to move the anvil retainer proximally to move the anvil assembly from an open position to a partially clamped position in which the threaded outer portion of the anvil retainer is engaged with the clamp gear, and activation of the second drive assembly through a second clamping stage moves the anvil retainer further proximally to move the anvil assembly from the partially clamped position to a fully clamped position.

10. The surgical stapling device of claim 9, wherein the shell assembly includes a clamp nut supported within the clamp gear, the clamp nut defining a threaded bore, the threaded outer portion of the anvil retainer received within the threaded bore of the clamp nut when the anvil assembly is in the partially clamped position.

11. The surgical stapling device of claim 10, wherein the anvil shaft is releasably coupled to the anvil retainer.

12. The surgical stapling device of claim 9, further including a handle assembly, the proximal portion of the adapter assembly coupled to the handle assembly.

13. A surgical stapling device comprising:
an adapter assembly including:
a flexible outer tube having a proximal portion and a distal portion;
a first drive assembly extending through the flexible outer tube, the first drive assembly including a flexible approximation link having a proximal portion and a distal portion, and an anvil retainer secured to the distal portion of the flexible articulation link, the anvil retainer including a threaded outer portion; and
a second drive assembly extending through the flexible outer tube, the second drive assembly including a flexible drive shaft having a proximal portion and a distal portion, and an input gear secured to the distal portion of the flexible drive shaft;
a tool assembly secured to the distal portion of the flexible outer tube, the tool assembly including:
an anvil assembly including an anvil head and an anvil shaft secured to the anvil head;
a shell assembly including a shell housing defining a cavity, a staple cartridge supported on the shell housing, a segmented pusher assembly, a pusher drive, and a clamp gear supported within the housing of the shell assembly, the clamp gear engaged with the input gear of the second drive assembly, the staple cartridge defining staple receiving slots that receive staples, the segmented pusher assembly positioned within the cavity of the shell housing and including a plurality of pushers arranged in an annular configuration, each of the pushers including an angled cam surface and being movable independently of other pushers of the plurality of pushers from a retracted position to an advanced position to eject the staples from the staple cartridge, the pusher drive supported within the cavity of the shell housing and including a cam member, the pusher drive being rotatable to move the cam member into sequential engagement with the angled cam surfaces of the plurality of pushers of the segmented pusher assembly to sequentially advance the plurality of pushers of the segmented pusher assembly from their retracted positions to their advanced positions;
wherein activation of the first drive assembly through a first clamping stage retracts the flexible approximation link to move the anvil retainer proximally to move the anvil assembly from an open position to a partially clamped position in which the threaded outer portion of the anvil retainer is engaged with the clamp gear, and activation of the second drive assembly through a second clamping stage moves the anvil retainer further proximally to move the anvil assembly from the partially clamped position to a fully clamped position.

14. The surgical stapling device of claim 13, further including a threaded spline tube secured within the shell housing, the pusher drive rotatably positioned about the threaded spline tube.

15. The surgical stapling device of claim 14, wherein the pusher drive includes a central hub that includes an inner threaded surface and the threaded spline tube has an outer surface that includes threads, the threads on the outer surface of the threaded spline tube being engaged with the inner threaded surface of the pusher drive such that rotation of the pusher drive about the threaded spline tube causes longitudinal movement of the pusher drive about the threaded spline tube.

16. The surgical stapling device of claim 15, wherein the angled cam surfaces of the plurality of pushers are longitudinally offset from each other in stepped fashion to compensate for the longitudinal movement of the pusher drive.

17. The surgical stapling device of claim 16, wherein the shell assembly includes a sun gear, a first planetary gear set, a spider input gear, a second planetary gear set, and a spider output gear, the first planetary gear set rotatably supported on the spider input gear, the second planetary gear set supported on the spider output gear, and the sun gear is engaged with the first planetary gear set, wherein rotation of the sun gear causes rotation of the first planetary gear set, which causes rotation of the spider gear input, which causes rotation of the second planetary gear set, which causes rotation of the spider output gear.

18. The surgical stapling device of claim 17, wherein the shell assembly includes a ring gear that is fixedly secured to the shell housing, the ring gear being engaged with the first and second planetary gear sets such that rotation of the first planetary gear set causes rotation of the spider input gear and rotation of the second planetary gear set causes rotation of the spider output gear.

19. The surgical stapling device of claim 18, wherein the shell assembly includes a clamp nut supported within the clamp gear, the clamp nut defining a threaded bore, the threaded outer portion of the anvil retainer received within the threaded bore of the clamp nut when the anvil assembly is in the partially clamped position.

20. The surgical stapling device of claim 18, further including a handle assembly, the proximal portion of the adapter assembly coupled to the handle assembly.

* * * * *